US008273576B2

United States Patent
Van Der Boom et al.

(10) Patent No.: US 8,273,576 B2
(45) Date of Patent: Sep. 25, 2012

(54) HEXAVALENT CHROMIUM DETECTOR

(75) Inventors: Milko E. Van Der Boom, Rishon LeZion (IL); Tarkeshwar Gupta, Rehovot (IL); Graham De Ruiter, Rehovot (IL)

(73) Assignee: Yeda Research and Development Co., Ltd., Rehovot (IL)

( * ) Notice: Subject to any disclaimer, the term of this patent is extended or adjusted under 35 U.S.C. 154(b) by 0 days.

(21) Appl. No.: 12/865,804

(22) PCT Filed: Feb. 1, 2009

(86) PCT No.: PCT/IL2009/000122
§ 371 (c)(1),
(2), (4) Date: Nov. 22, 2010

(87) PCT Pub. No.: WO2009/095924
PCT Pub. Date: Aug. 6, 2009

(65) Prior Publication Data
US 2011/0059536 A1    Mar. 10, 2011

Related U.S. Application Data

(60) Provisional application No. 61/025,169, filed on Jan. 31, 2008.

(51) Int. Cl.
*G01N 33/20* (2006.01)
*G01N 21/00* (2006.01)
*C07F 15/00* (2006.01)

(52) U.S. Cl. ................. 436/83; 436/84; 436/73; 546/2

(58) Field of Classification Search .............. 436/73, 436/83, 84; 422/82.05; 546/2
See application file for complete search history.

(56) References Cited

FOREIGN PATENT DOCUMENTS
WO        2006/085319 A      8/2006
WO     WO/2006/085319    *   8/2006

OTHER PUBLICATIONS

Flow Injection Fluorimetric Determination of Chromium VI in Electroplating Baths by Luminescence Quenching of tris(2,2'- bipyridyl) ruthenium II. Saad S.M. Hassan, Ayman A. Abdel-Shafi, Ayman H.K. Mohammed Talanta 67 (2005) 696-702.*
Hassan S. S. M. et al: "Flow Injection Fluorimetric Determination of Chromium(VI) in Electroplating Baths by Luminescence Quenching of Tris (2,2'-bipyridyl) Ruthenium(I I)", Talanta, vol. 67, No. 4, pp. 696-702 (2005).
Du G et al: "Kinetics of the Reaction of Chromium(VI) with Tris(1,10-Phenanthroline)iron(II) Ions in Acidic Solutions. Anion and Medium Effects: Perchlorate versus Triflate", Inorganic Chemistry, vol. 45, No. 3, pp. 1053-1058 (2006).

(Continued)

*Primary Examiner* — Vickie Kim
*Assistant Examiner* — Dwan A Gerido
(74) *Attorney, Agent, or Firm* — Browdy and Neimark, PLLC

(57) ABSTRACT

The present invention relates to a molecular-based system for the optical detection, quantification and detoxification of hexavalent chromium ($Cr^{6+}$) by reversible metal-substrate electron transfer. More particularly, the invention provides a $Cr^{6+}$ sensor device comprising a divalent osmium ($Os^{2+}$)-, iron ($Fe^{2+}$)- or ruthenium ($R^{2+}$)-based pyridyl complex capable of changing its oxidation state in response to a reduction of $Cr^{6+}$ at the presence of $H^+$, thereby causing a reversible and optically readable change in optical properties of said complex. The $Os^{2+}$-, $Fe^{2+}$- or $R^{2+}$-based pyridyl complex used according to the invention can be used for selective detection and quantification of $Cr^{6+}$, as well as for catalytic detoxification of $Cr^{6+}$.

26 Claims, 14 Drawing Sheets

OTHER PUBLICATIONS

Yonehara N et al: "Indirect Kinetic Spectrophotometric Determination of Antimony(III) by the Oxidation Reaction of Tris(1,10-phenanthroline)iron(II) by Excess Chromium (VI)", Reports of the Faculty of Science / Kagoshima University, No. 17, pp. 19-23 (1984).

Yonehara N et al: "Kinetic Spectrophotometric Determination of Antimony(III) Based on Induced Oxidation of Tris (1,10-Phenanthroline)Iron(II) by Chromium ( VI )", Analytica Chimica Acta, vol. 143, pp. 277-281 (1982).

Dutt V V S E et al: "Analytical Applications of Reaction-Rate-Promoting Effects. Tris(1,10-Phenanthroline)Iron(II) Chromium ( VI ) Indicator Reaction", Analytical Chemistry, vol. 46, No. 8, pp. 1090-1094 (1974).

Yamamoto Y et al: "Spectrophotometric Determination of Anions by Solvent Extraction with Metal Chelate Cations. XLVI. Spectrophotometric Determination of Chromium ( VI ) by Solvent Extraction with Tris(1,10-Phenanthroline)Iron (II) Chelate Cation", Bunseki Kagaku—Japan Analyst, vol. 19, No. 9, pp. 1168-1174 (1970).

Espenson J H et al: "Kinetics and Mechanisms of Reactions of Chromium ( VI ) and Iron(II) Species in Acidic Solution", Journal of the American Chemical Society, vol. 85, No. 21, pp. 3328-3333 (1963).

* cited by examiner

HEXAVALENT CHROMIUM DETECTOR

TECHNICAL FIELD

The present invention relates to a molecular-based system, more particularly, to a divalent osmium-, iron- or ruthenium-based pyridyl complex, for the optical detection, quantification and detoxification of $Cr^{6+}$ by reversible metal-substrate electron transfer.

BACKGROUND ART

The most remarkable occurrence of chromium in nature is found in ruby and emerald gemstones, where replacing $Al^{3+}$ by $Cr^{3+}$ produces the characteristic red and green colors of the ruby and emerald gemstones, respectively. Chromium exists in oxidation states ranging from $Cr^{2+}$—$Cr^{6+}$, wherein $Cr^{3+}$ is thermodynamically the most stable and also the most important, being an essential trace element with a daily uptake of approximately 25-50 μg. However, in the higher oxidation states, e.g., as $Cr^{6+}$, it is extremely dangerous being 500-1000 times more toxic than $Cr^{3+}$. Long term exposure to $Cr^{6+}$ can lead to lung cancer, chronic bronchitis, asthma, emphysema, pulmonary fibrosis and other kinds of diseases (Reynolds et al., 2007; Zhitkovich, 2005; Levina and Lay, 2005). According to the US Department of Health and Human Services, the maximum exposure limit in air varies between 0.5-100 μg/m$^3$, whereas in water the maximum exposure limit is 100 μg/l (ATSDR *Chromium Toxicity*, US Department of Health and Human Services, 2000).

The main sources for $Cr^{6+}$ are modern chemical and industrial processes including oil and coal combustion, manufacturing of textile dyes, fabrication of nuclear weapons, chrome plating, metal finishing, and leather and wood preservation. These processes create a vast amount of toxic waste (Singh and Gupta, 2007; Liu et al., 2006; Gheju and Iovi, 2006; Mytych and Stasicka, 2004; Kieber et al., 2002). For example, the United States annually emits tons of $Cr^{6+}$ as atmospheric pollution. Besides that, there is additional pollution of $Cr^{6+}$ as waste water (ATSDR *Chromium Toxicity*, US Department of Health and Human Services, 2000). Therefore, selective detection and quantification, together with detoxification of $Cr^{6+}$, are of high importance.

Current detoxification of $Cr^{6+}$ is based on chemical reduction with stoichiometric amounts of iron(sulfur) salts followed by precipitation with a base (Eary and Rai, 1988; EPA, 1980, 2000). Although several sophisticated techniques are available to detect and quantify $Cr^{6+}$ (Marqués et al., 2000), a selective and cost-effective sensor system with minimum requirements for sample preparation is highly desirable. Alternative approaches are rare (Boiadjiev et al., 2005; Tian et al., 2005; Turyan and Mandler, 1997; Ji et al., 2001). $Cr^{6+}$ undergoes reduction in solution in the presence of $H^+$ and low-valent metal centers such as $Fe^{2+}$, $Mn^{2+}$, $V^{3+}$ or $Os^{2+}$ (Espenson, 1970; Davies and Espenson, 1970; Birk, 1969; Westheimer, 1949). For example, $[Os(bpy)_3]Cl_2$ reacts with $K_2Cr_2O_7$ in water under acidic conditions (pH=1) to afford $Cr^{3+}$, as may be indicated by electron spin resonance (ESR) spectroscopy. Monolayer chemistry is rapidly developing (Collman et al., 2007; Yerushalmi et al., 2004; Liu et al., 2003; Lahann et al., 2003; Gupta and van der Boom, 2006, 2007; Gupta et al., 2006, 2007; Baker et al., 2006; Gulino et al., 2005; Basabe-Desmonts et al., 2004; Ashkenasy et al., 2000; Crooks and Ricco, 1998), and such, well-designed interfaces have been used to detect various analytes (Gupta and van der Boom, 2006, 2007; Gupta et al., 2006, 2007; Baker et al., 2006; Gulino et al., 2005; Basabe-Desmonts et al., 2004; Ashkenasy et al., 2000; Crooks and Ricco, 1998). However, the design of a suitable platform for detecting specific metal ions in a matrix remains a challenging task (Gupta and van der Boom, 2007; Zhang et al., 2006).

International Publication No. WO 2006085319 and the corresponding US Publication No. 20070258147, herewith incorporated by reference in their entirety as if fully disclosed herein, disclose a device having reversibly changeable and optically readable optical properties, the device comprising a substrate having an electrically conductive surface and carrying a redox-active layer structure configured to have at least one predetermined electronic property including at least one of electrodensity and oxidation state, said at least one electronic property being changeable by subjecting the layer structure to an electric field, wherein the electronic property of the layer structure defines an optical property of the structure thereby determining an optical response of the structure to certain incident light, the device enabling to effect a change in said electronic property that results in a detectable change in the optical response of the layer structure.

The aforesaid US 20070258147 further discloses a sensor device configured and operable for sensing at least one predetermined cation, anion, radical, liquid or gas substance, the device comprising a redox-active layer structure selected to be capable of changing its oxidation state in response to a reaction with said at least one substance, thereby causing a change in optical properties of said structure, said change being reversible and being optically readable. As defined in the aforesaid US publication, the cation to be recognized said sensor device may be selected from the group consisting of $[Ru(phen)_3]^{3+}$, $[Ru(bipy)_3]^{3+}$, $[trianthrene]^+$, $[Fe(bipy)_3]^{3+}$, $Pu^{4+}$, $Au^+$, $Ag^{2+}$, $Ag^+$, $Ce^{4+}$, $Ru^{3+}$, $Ir^{3+}$, $Ir^{4+}$, $Rh^+$, $Rh^{2+}$, $U^{2+}$, $U^{3+}$, $U^{4+}$, $U^{5+}$, $Rh^{3+}$, $Pd^{2+}$, $Pd^{4+}$, $Pt^{2+}$, $Pt^{4+}$, $Ni^{2+}$, $Ni^{4+}$, $Co^{3+}$, $Hg^{2+}$, $Cu^{2+}$, $Cu^+$, $Cd^{2+}$, $Pb^{2+}$, $Pb^{4+}$, $Sn^{2+}$, $Sn^{4+}$, $W^+$, $NO^+$, $Fe^{2+}$, $Fe^{3+}$, an actinide and a lanthanide cation. In a particular embodiment, the redox-active layer structure of said sensor device comprises the osmium polypyridyl compound bis(2,2'-bipyridine)[4'-methyl-4-(2-(4-(3-propyltrimethoxysilane)pyridinium)ethenyl)-2,2'-bipyridine]osmium(II)[tris(hexafluorophosphate)/tri-iodide], respectively.

SUMMARY OF INVENTION

It has been found, in accordance with the present invention, that divalent osmium-based pyridyl complexes, in particular, (bis(2,2'-bipyridine)[4'-methyl-4-(2-(4-(3-propyltrimethoxysilane)pyridinium)ethenyl)-2,2'-bipyridine]osmium(II)[tris(hexafluorophosphate)/tri-iodide], previously disclosed in WO 2006085319, and bis(2,2'-bipyridine)[4'-methyl-4-(2-(4-(3-propoxytrimethoxysilane)phenyl)ethenyl)-2,2'-bipyridine]osmium(II) [bis(hexafluorophosphate)/di-iodide], are able to selectively detect and quantify traces, i.e., ppm levels, of hexavalent chromium ($Cr^{6+}$) in $H_2O$ and MeCN under acidic conditions. The measurements are relatively fast, i.e., about 1-min, and can be carried out under environmental conditions and monitored in- and ex-situ using standard UV/visible spectroscopy (260-900 nm). The combined physicochemical properties and device performance of such pyridyl complex-based monolayers, including robustness, regeneration, response time, stability and selectivity, as well as the low detection limits, make this system an excellent alternative for detecting and quantifying $Cr^{6+}$. Since osmium, iron and ruthenium belong to the same group of chemical elements, i.e., have similar physicochemical properties, it is postulated that divalent iron/ruthenium-based pyridyl complexes will have a similar capacity.

Thus, in one aspect, the present invention relates to a hexavalent chromium ($Cr^{6+}$) sensor device comprising a divalent osmium ($Os^{2+}$)-, iron ($Fe^{2+}$)- or ruthenium ($Ru^{2+}$)-based pyridyl complex capable of changing its oxidation state in response to a reduction of $Cr^{6+}$ at the presence of $H^+$, thereby causing a reversible and optically readable change in optical properties of said complex. The device of the present invention may further comprise a substrate carrying a layered structure of said pyridyl complex.

In another aspect, the present invention relates to an acidic aqueous solution comprising a divalent osmium ($Os^{2+}$)-, iron ($Fe^{2+}$)- or ruthenium ($Ru^{2+}$)-based pyridyl complex capable of changing its oxidation state in response to a reduction of $Cr^{6+}$ at the presence of $H^+$, for selective detection and quantification of $Cr^{6+}$.

In further aspects, the present invention relates to an ampoule containing an acidic aqueous solution as defined above; as well as to a kit containing at least two such ampoules.

In yet another aspect, the present invention provides a method for selective detection and quantification of $Cr^{6+}$ in a liquid sample, comprising:
(i) exposing a divalent osmium ($Os^{2+}$)-, iron ($Fe^{2+}$)- or ruthenium ($Ru^{2+}$)-based pyridyl complex capable of changing its oxidation state in response to a reduction of $Cr^{6+}$ to said sample, for a sufficient time period at the presence of $H^+$;
(ii) recording absorption spectra of said pyridyl complex at the UV/visible spectral range, preferably at the range of 400-900 nm; and
(iii) monitoring the presence of $Cr^{6+}$ in said sample and determining its concentration according to the change in the absorption spectra of (ii) compared to a predetermined absorption spectra of said pyridyl complex.

In still a further aspect, the present invention provides a method for detoxification of $Cr^{6+}$ in an aqueous or organic liquid media, comprising:
(i) contacting said liquid media with a divalent osmium ($Os^{2+}$)-, iron ($Fe^{2+}$)- or ruthenium ($Ru^{2+}$)-based pyridyl complex capable of changing its oxidation state to $Os^{3+}$-, $Fe^{3+}$- or $Ru^{3+}$-based pyridyl complex, respectively, in response to a reduction of $Cr^{6+}$, for a sufficient time period at the presence of $H^+$, wherein said pyridyl complex is carried as a layered structure on a substrate;
(ii) monitoring the presence of $Cr^{6+}$ and determining its concentration in a sample taken from said liquid media; and
(iii) when $Cr^{6+}$ is detected in said sample, reducing said $Os^{3+}$-, $Fe^{3+}$- or $Ru^{3+}$-based pyridyl complex and repeating steps (i) and (ii).

In yet a further aspect, the present invention provides a catalytic process for reduction of $Cr^{+6}$, comprising reducing said $Cr^{6+}$ with a divalent osmium ($Os^{2+}$)-based pyridyl complex to thereby oxidize the $Os^{2+}$ to $Os^{3+}$, and exposing the oxidized $Os^{3+}$ to water for a sufficient time period to thereby regenerate the $Os^{3+}$ to $Os^{2+}$.

MODES FOR CARRYING OUT THE INVENTION

Figure 1:
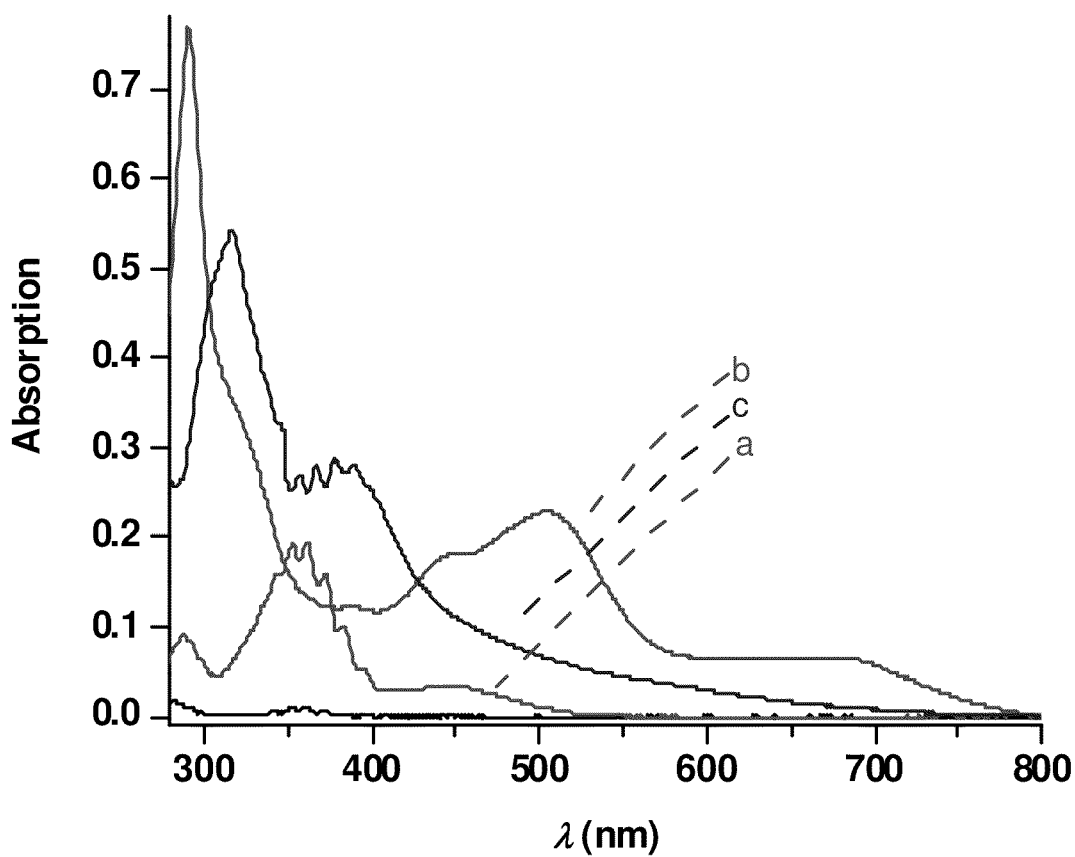
FIG. 1 shows absorption spectra of (a) a solution (pH 1) of (0.85 mM) $Cr^{6+}$ in MeCN; (b) a solution of 10.4 μM compound 10 in MeCN; and (c) a mixed solution of 1 ml (20.8 μM) compound 10 and 1 ml (1.7 mM) $Cr^{6+}$, both in MeCN at pH 1.

In one aspect, the present invention relates to a $Cr^{6+}$ sensor device comprising a divalent osmium ($Os^{2+}$)-, iron ($Fe^{2+}$)- or ruthenium ($Ru^{2+}$)-based pyridyl complex capable of changing its oxidation state in response to a reduction of $Cr^{6+}$ at the presence of $H^+$, thereby causing a reversible and optically readable change in optical properties of said complex. In a preferred embodiment, the sensor device of the present invention comprises $Os^{2+}$-based pyridyl complex.

The term "oxidation state", as used herein, refers to the electrically neutral state or to the state produced by the gain or loss of electrons to an element, compound or chemical substituent/subunit. In a preferred embodiment, this term refers to states including the neutral state and any state other than a neutral state caused by the gain or loss of electrons (reduction or oxidation).

The term "optical properties", as used herein, refers to the absorption spectrum of the $Os^{2+}$-, $Fe^{2+}$- or $Ru^{2+}$-based pyridyl complex used in the $Cr^{6+}$ sensor device of the present invention. The change in the optical properties is caused electrochemically by addition or withdrawal of one or more electrons to or from the $Os^{2+}$-, $Fe^{2+}$- or $Ru^{2+}$-based pyridyl complex.

The term "pyridyl complex", as used herein, refers to a metal having one or more pyridyl ligands, i.e., the $Os^{2+}$-, $Fe^{2+}$- or $Ru^{2+}$-based pyridyl complex used in the $Cr^{6+}$ sensor device of the present invention may be any pyridyl complex in which $Os^{2+}$, $Fe^{2+}$ or $Ru^{2+}$ is coordinated to one or more pyridyl ligands.

In one embodiment, the $Os^{2+}$-, $Fe^{2+}$- or $Ru^{2+}$-based pyridyl complex is charged tris-bipyridyl $Os^{2+}$, $Fe^{2+}$ or $Ru^{2+}$-complex or a derivative thereof. More preferably, the $Os^{2+}$-, $Fe^{2+}$- or $Ru^{2+}$-based pyridyl complex is a compound of the general formula I:

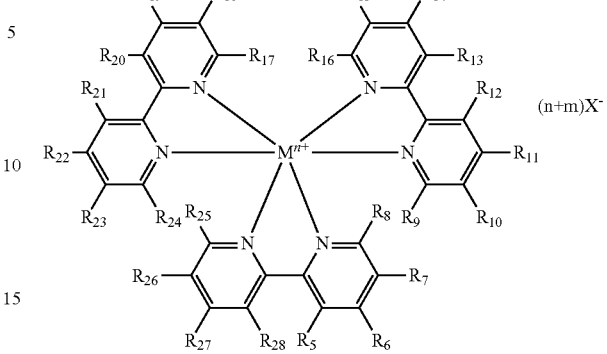

wherein M is Os, Fe or Ru; n is the formal oxidation state of the Os or Fe, wherein n is 2 or 3; m is the positive charge of the tris-bipyridyl ligand, wherein m is an integer from 0 to 24, X is a counter anion selected from $Br^-$, $Cl^-$, $F^-$, $I^-$, $PF_6^-$, $BF_4^-$, $OH^-$, $ClO_4^-$, $SO_3^-$, $CF_3COO^-$, $CN^-$, alkyl$COO^-$, aryl-$COO^-$ or a combination thereof; and $R_5$ to $R_{28}$ is each independently selected from hydrogen, halogen, hydroxyl, azido, nitro, cyano, amino, substituted amino, thiol, $C_1$-$C_{10}$ alkyl, cycloalkyl, heterocycloalkyl, haloalkyl, aryl, heteroaryl, alkoxy, alkenyl, alkynyl, carboxamido, substituted carboxamido, carboxyl, protected carboxyl, protected amino, sulfonyl, substituted aryl, substituted cycloalkyl or substituted heterocycloalkyl, wherein at least one of said $R_5$ to $R_{28}$ is a group A or B:

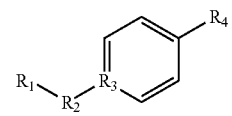

wherein

A is linked to the ring structure of the compound of general formula I via $R_4$; $R_4$ is selected from cis/trans C=C, C≡C, N=N, C=N, N=C, C—N, N—C, alkylene, arylene or a combination thereof; $R_3$ is C or N; $R_2$ is absent or is selected from hydrogen, alkyl, alkylene, aryl, arylene, OH, O-alkyl, O-alkylene or a combination thereof; and $R_1$ is absent or is selected from hydrogen, trialkoxysilane, trihalidesilane, thiol, COOH, $COO^-$, $Si(OH)_3$ or phosphonate; and B is —$O(CH_2)_p$—$R_{29}$ linked to the ring structure of the compound of general formula I via the oxygen, wherein p is an integer from 9 to 12; and $R_{29}$ is selected from hydrogen, trialkoxysilane, trihalidesilane, thiol, COOH, $COO^-$, $Si(OH)_3$ or phosphonate; and any two vicinal $R_5$-$R_{28}$ substituents, together with the carbon atoms to which they are attached, may form a fused ring system selected from cycloalkyl, heterocycloalkyl, heteroaryl or aryl, wherein said fused system may be substituted by one or more groups selected from $C_1$-$C_{10}$ alkyl, aryl, azido, cycloalkyl, halogen, heterocycloalkyl, alkoxy, hydroxyl, haloalkyl, heteroaryl, alkenyl, alkynyl, nitro, cyano, amino, substituted amino, carboxamido, substituted carboxamido, carboxyl, protected carboxyl, protected amino, thiol, sulfonyl or substituted aryl; and said fused ring system may also contain at least one heteroatom selected from N, O or S.

The term "alkyl", as used herein, typically means a straight or branched hydrocarbon radical having preferably 1-10 carbon atoms, and includes, e.g., methyl, ethyl, n-propyl, isopropyl, n-butyl, isobutyl, sec-butyl, tert-butyl, n-pentyl, isopentyl, 2,2-dimethylpropyl, n-hexyl, n-heptyl, n-octyl, n-nonyl, n-decyl and the like. The alkyl may further be substituted. The term "alkylene" refers to a linear divalent hydrocarbon chain having preferably 1-10 carbon atoms and includes, e.g., methylene, ethylene, propylene, butylene, pentylene, hexylene, octylene and the like.

The term "alkenyl" typically means a straight or branched hydrocarbon radical having preferably 2-10 carbon atoms and one or more double bonds. Non-limiting examples of such alkenyls are ethenyl, 3-buten-1-yl, 2-ethenylbutyl, 3-octen-1-yl, and the like. The term "alkenylene" refers to a linear divalent hydrocarbon chain having preferably 2-10 carbon atoms and one or more double bonds, and includes, e.g., 1-propylene, 1-butylene, 2-butylene, 3-hexylene and the like.

The term "alkynyl" refers to a straight or branched hydrocarbon radical having preferably 2-10 carbon atoms and containing at least one triple bond.

The term "cycloalkyl" typically means a saturated aliphatic hydrocarbon in a cyclic form (ring) having preferably 3-10 carbon atoms. Non-limiting examples of such cycloalkyl ring systems include cyclopropyl, cyclobutyl, cyclopentyl, cyclohexyl, cyclodecyl and the like. The cycloalkyl may be fused to other cycloalkyls, such in the case of cis/trans decalin. The term "heterocycloalkyl" refers to a cycloalkyl, in which at least one of the carbon atoms of the ring is replaced by a heteroatom selected from N, O or S.

The term "alkylCOO" refers to an alkyl group substituted by a carboxyl group (—COO—) on any one of its carbon atoms. Preferably, the alkyl has 1-10 carbon atoms, more preferably $CH_3COO^-$.

The term "aryl" typically means any aromatic group, preferably having 6-14 carbon atoms such as phenyl and naphtyl. The aryl group may be substituted by any known substituents. The term "arylCOO" refers to such a substituted aryl, in this case being substituted by a carboxylate group.

The term "heteroaryl" refers to an aromatic ring system in which at least one of the carbon atoms is replaced by a heteroatom selected from N, O or S. Non-limiting examples of heteroaryl include pyrrolyl, furyl, thienyl, pyrazolyl, imidazolyl, oxazolyl, isoxazolyl thiazolyl, isothiazolyl, pyridyl, 1,3-benzodioxinyl, pyrazinyl, pyrimidinyl, 1,3,4-triazinyl, 1,2,3-triazinyl, 1,3,5-triazinyl, thiazinyl, quinolinyl, isoquinolinyl, benzofuryl, isobenzofuryl, indolyl, imidazo[1,2-a]pyridyl, pyrido[1,2-a]pyrimidinyl, benz-imidazolyl, benzthiazolyl and benzoxazolyl.

The term "halogen" includes fluoro, chloro, bromo, and iodo. The term "haloalkyl" refers to an alkyl substituted by at least one halogen.

The term "alkoxy" refers to the group —OR, wherein R is an alkyl group. The term "azido" refers to —$N_3$. The term "nitro" refers to —$NO_2$ and the term "cyano" refers to —CN. The term "amino" refers to the group —$NH_2$ or to substituted amino including secondary, tertiary and quaternary substitutions wherein the substituents are alkyl or aryl. The term "protected amino" refers to such groups which may be converted to the amino group. The term "carboxamido" refers to the group —$CONH_2$ or to such a group substituted, in which each of the hydrogens is replaced by an alkyl or aryl group.

The term "carboxyl" refers to the group —COOH. The term "protected carboxyl" refers to such groups which may be converted into the carboxyl group, e.g., esters such as —COOR, wherein R is an alkyl group or an equivalent thereof, and others which may be known to a person skilled in the art of organic chemistry.

The term "trialkoxysilane" refers to a group of the general formula —$Si(OR)_3$, wherein each of the three R groups is an alkyl group, and may be the same or different, preferably, trimethoxysilane or triethoxysilane. Similarly, the term "trihalidesilane" refers to —$SiX_3$, wherein X is a halogen, each X may be same or different.

The expression "any two vicinal $R_5$-$R_{28}$ substituents" refers to any two substituents on the benzene rings, being ortho to one another. The expression "fused ring system" refers to at least two rings sharing one bond, such as in the case of naphthalene, phenanthrene, benzindole, benzpyridine and others. The fused ring system contains at least one benzene ring, being the ring of the compound of general formula I and another ring being formed by the ring closure of said any two vicinal $R_4$-$R_{27}$ substituents. The said another ring may be saturated or unsaturated, substituted or unsubstituted and may be heterocylic.

The compounds described in the specification, both the compounds of formula I, i.e., the $Os^{2+}$-, $Fe^{2+}$- or $Ru^{2+}$-based pyridyl complexes/compounds, as well as the starting compounds and intermediates, are herein identified by the Arabic numbers 1-15 in bold. However, since the pyridyl complexes specifically described herein are defined with two different anions, each one of the compounds 4-15 has two forms designated "a" and "b".

In one embodiment, the pyridyl complex is the compound of the general formula I as defined above, wherein M is Os, Fe or Ru, n is 2, m is 0, X is $PF_6^-$ or $I^-$, $R_5$, $R_7$ to $R_{26}$ and $R_{28}$ each is hydrogen, $R_6$ is methyl, and $R_{27}$ is A, wherein $R_4$ is C=C, $R_3$ is N, and $R_2$ and $R_1$ are both absent, i.e., bis(2,2'-bipyridine)[4'-methyl-4-(2-(4-pyridyl)ethenyl)-2,2'-bipyridine]osmium(II)[bis(hexafluorophosphate)/di-iodide], herein designated compounds 4a-4-b, respectively; bis(2,2'-bipyridine)[4'-methyl-4-(2-(4-pyridyl)ethenyl)-2,2'-bipyridine]iron(II)[bis(hexafluorophosphate)/di-iodide], herein designated compounds 5a-5b, respectively; or bis(2,2'-bipyridine)[4'-methyl-4-(2-(4-pyridyl)ethenyl)-2,2'-bipyridine]ruthenium(II)[bis-(hexafluorophosphate)/di-iodide], herein designated compounds 6a-6b, respectively.

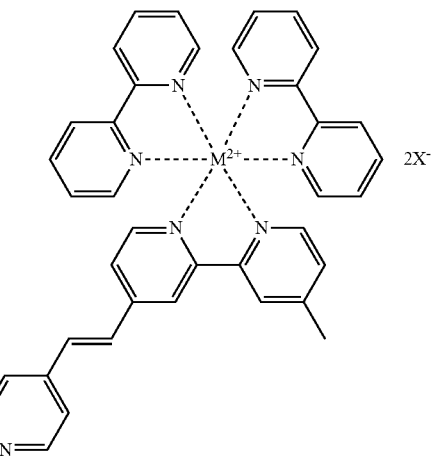

4a - M = Os; X = $PF_6^-$
4b - M = Os; X = $I^-$
5a - M = Fe; X = $PF_6^-$
5b - M = Fe; X = $I^-$
6a - M = Ru; X = $PF_6^-$
6b - M = Ru; X = $I^-$

In another embodiment, the pyridyl complex is the compound of the general formula I as defined above, wherein M is Os, Fe or Ru, n is 2, m is 1, X is $PF_6^-$ or $I^-$, $R_5$, $R_7$ to $R_{26}$ and $R_{28}$ each is hydrogen, $R_6$ is methyl, and $R_{27}$ is A, wherein $R_4$ is C=C, $R_3$ is N, $R_2$ is methyl, and $R_1$ is absent, i.e., bis(2,2'-bipyridine)[4'-methyl-4-(2-(4-methylpyridinium)ethenyl)-2,2'-bipyridine]osmium(II)[tris(hexafluorophosphate)/tri-iodide], herein designated compounds 7a-7b, respectively; bis(2,2'-bipyridine)[4'-methyl-4-(2-(4-methylpyridinium)ethenyl)-2,2'-bipyridine]iron(II)[tris(hexafluorophosphate)/tri-iodide], herein designated compounds 8a-8b, respectively; or bis(2,2'-bipyridine)[4'-methyl-4-(2-(4-methylpyridinium)ethenyl)-2,2'-bipyridine]ruthenuim(II)[tris(hexafluorophosphate)/tri-iodide], herein designated compounds 9a-9b, respectively.

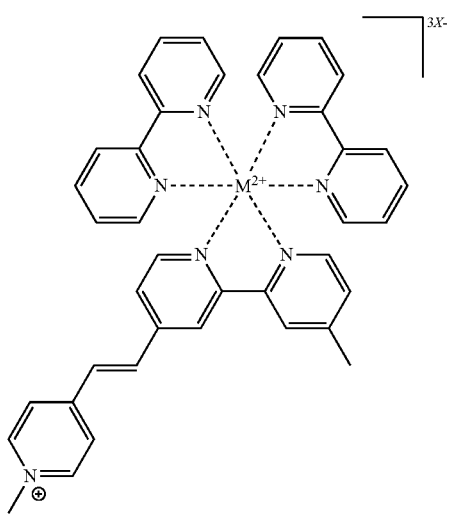

7a - M = Os; X = $PF_6^-$
7b - M = Os; X = $I^-$
8a - M = Fe; X = $PF_6^-$
8b - M = Fe; X = $I^-$
9a - M = Ru; X = $PF_6^-$
9b - M = Ru; X = $I^-$

In a preferred embodiment, the pyridyl complex is the compound of the general formula I as defined above, wherein M is Os, n is 2, m is 1, X is $PF_6^-$ or $I^-$, $R_5$, $R_7$ to $R_{26}$ and $R_{28}$ each is hydrogen, $R_6$ is methyl, and $R_{27}$ is A, wherein $R_4$ is C=C, $R_3$ is N, $R_2$ is propyl, and $R_1$ is trimethoxysilane, i.e., bis(2,2'-bipyridine)[4'-methyl-4-(2-(4-(3-propyltrimethoxysilane)pyridinium)ethenyl)-2,2'-bipyridine]osmium(II)[tris(hexafluorophosphate)/tri-iodide], herein designated compounds 10a and 10b, respectively.

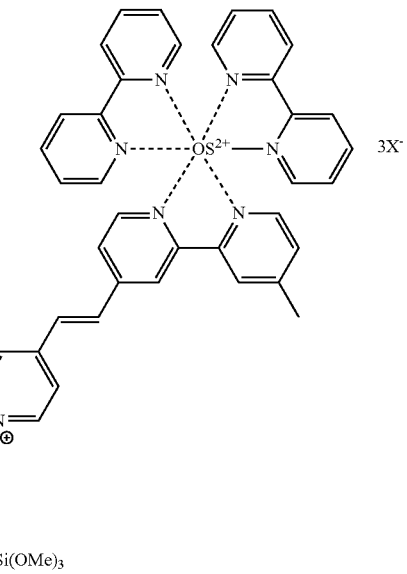

10a - X = $PF_6^-$
10b - X = $I^-$

In a further embodiment, the pyridyl complex is the compound of the general formula I as defined above, wherein M is Os, Fe or Ru, n is 2, m is 0, X is $PF_6^-$ or $I^-$, $R_5$, $R_7$ to $R_{26}$ and $R_{28}$ each is hydrogen, $R_6$ is methyl, and $R_{27}$ is A, wherein $R_4$ is C=C, $R_3$ is C, $R_2$ is OH, and $R_1$ is absent, i.e., bis(2,2'-bipyridine)[4'-methyl-4-(2-(4-hydroxyphenyl)ethenyl)-2,2'-bipyridine]osmium(II)[bis(hexafluorophosphate)/di-iodide], herein designated compounds 11a-11b, respectively; bis(2,2'-bipyridine)[4'-methyl-4-(2-(4-hydroxyphenyl)ethenyl)-2,2'-bipyridine]iron(II)[bis(hexafluorophosphate)/di-iodide], herein designated compounds 12a-12b, respectively; or bis(2,2'-bipyridine)[4'-methyl-4-(2-(4-hydroxyphenyl)ethenyl)-2,2'-bipyridine]ruthenium(II)[bis(hexafluorophosphate)/di-iodide], herein designated compounds 13a-13b, respectively.

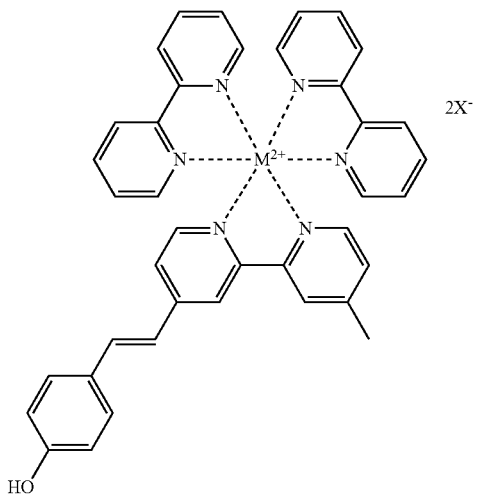

11a - M = Os; X = $PF_6^-$
11b - M = Os; X = $I^-$
12a - M = Fe; X = $PF_6^-$
12b - M = Fe; X = $I^-$
13a - M = Ru; X = $PF_6^-$
13b - M = Ru; X = $I^-$

In another preferred embodiment, the pyridyl complex is the compound of the general formula I as defined above, wherein M is Os, n is 2, m is 0, X is $PF_6^-$ or $I^-$, $R_5$, $R_7$ to $R_{26}$ and $R_{28}$ each is hydrogen, $R_6$ is methyl, and $R_{27}$ is A, wherein $R_4$ is C≡C, $R_3$ is C, $R_2$ is O-propyl, and $R_1$ is trimethoxysilane, i.e., bis(2,2'-bipyridine)[4'-methyl-4-(2-(4-(3-propoxytrimethoxysilane)phenyl)ethenyl)-2,2'-bipyridine]osmium(II)[bis(hexafluorophosphate)/di-iodide], herein designated compounds 14a and 14b, respectively.

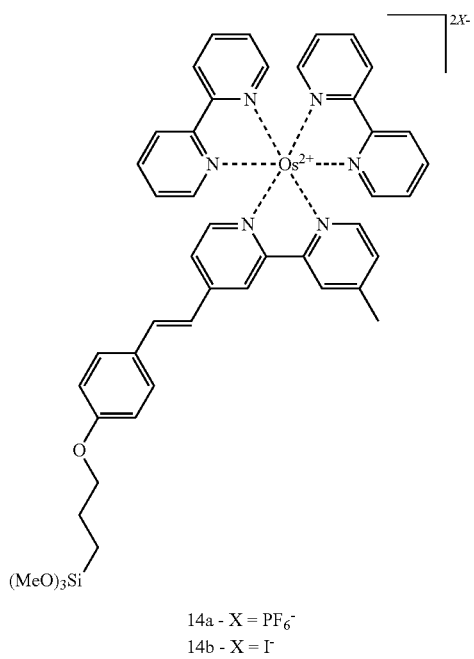

14a - X = $PF_6^-$
14b - X = $I^-$

In still further embodiments, the pyridyl complex is the compound of the general formula I as defined above, wherein M is Os, n is 2, m is 0, X is $PF_6^-$ or $I^-$, $R_5$, $R_7$ to $R_{26}$ and $R_{28}$ each is hydrogen, $R_6$ and $R_{27}$ each is B, wherein p is 9 and $R_{29}$ is triethoxysilane, i.e., bis(2,2'-bipyridine)[4,4'-dinonoxy-9-triethoxysilane-2,2'-bipyridine]osmium(II)[bis(hexafluorophosphate)/di-iodide], herein designated compounds 15a and 15b, respectively.

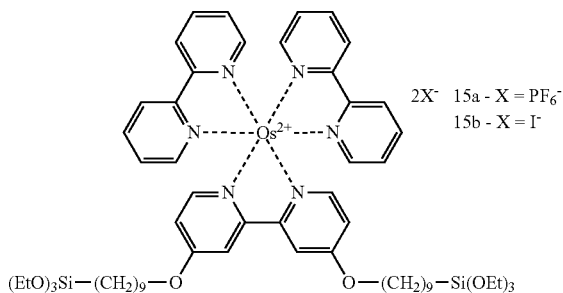

2X⁻  15a - X = $PF_6^-$
     15b - X = $I^-$

The various $Os^{2+}$-, $Fe^{2+}$- or $Ru^{2+}$-based pyridyl complexes used according to the present invention can be prepared by any suitable method known in the art, e.g., as disclosed in the aforesaid WO 2006085319 and US 20070258147. In particular, the preparation of the $Os^{2+}$-based pyridyl complex 10 used in all the experiments conducted in accordance with the present invention, as well as the formation of 10-based monolayers on glass, are further described in Examples 1-2 hereinafter.

As shown in detail in the Examples section, trace amounts of $Cr^{6+}$ in aqueous or organic solution could be detected in situ by monitoring the optical properties of the 10-based monolayer by UV/visible spectroscopy in the transmission mode (260-900 nm). For example, immersing a 10-based monolayer on glass (0.8×2.5×0.1 cm) in an acidified MeCN solution containing 0.5 ppm $Cr^{6+}$ resulted in a significant decrease of the absorption band at λ=293 nm and both singlet and triplet states of metal-to-ligand charge-transfer (MLCT) bands at λ=516 and 692 nm, and a concurrent increase of the ligand-to-metal charge-transfer (LMCT) band at λ=317 nm. Saturation of the sensor occurred under these reaction conditions after 45 min. The 10-based monolayer is stable in $H_2O$ at pH=1 for at least several hours in the absence of $Cr^{6+}$, as judged by UV/visible spectroscopy.

Remarkably, the amount of $Cr^{6+}$ could be accurately quantified within only 1-min of exposure time as well. The good linear correlation and the system stability allowed reliable and accurate quantification of $Cr^{6+}$. For instance, a blind test showed that even after several weeks in air, the calibrated 10-based sensor can be used to determine the amount of $Cr^{6+}$ within 10% accuracy. The detection range in $H_2O$ and MeCN was 1-100 ppm and 0.5-100 ppm, respectively. Reduction of the $Os^{3+}$ system by water completely restored the MLCT bands at λ=516 and 692 nm to their original values.

As further shown, the surface-solution redox chemistry is dependent on the pH and shows good reversibility for at least 10 redox cycles. Ex situ UV/visible follow-up experiments demonstrated that the system only responds to the analyte at a pH<3 for a 1-min exposure time, wherein the highest oxidation rate is observed at pH=0.3. Interestingly, reduction of the sensor with $H_2O$ was pH dependent as well. The maximum reduction rate was observed at pH=7.5, whereas at pH=1, hardly any reaction was observed. The monolayer setup became unstable at higher pH values, which is common for siloxane-based monolayers.

The selectivity of the 10-based monolayer towards $Cr^{6+}$ was demonstrated using a series of aqueous matrices containing various metal ions, or anions commonly found in groundwater. Only samples containing $Cr^{6+}$ induced significant optical changes (ΔA≧60%) after a 1-min exposure time.

Whereas in the absence of $H^+$, the 10-based sensor does not respond to $Cr^{6+}$, we recently reported that under such conditions, the 10-based monolayer is capable of optically sensing $Fe^{3+}$ in $H_2O$ and MeCN. Apparently, this dual sensor system is capable of detecting a specific metal ion by varying the pH. Time-dependent measurement of the oxidation of the 10-based monolayer by aqueous solutions containing 80 ppm $Fe^{3+}$ or $Cr^{6+}$ showed that the optical response of the sensor towards the latter ion is at least 6 times greater within 1-min of exposure time. Moreover, $Fe^{3+}$ can selectively be removed from the medium by treatment with strong base prior to analysis of the $Cr^{6+}$ content by the 10-based monolayer. $Cr^{6+}$ is stable under basic conditions.

The formation of device quality sensors requires not only the ability to detect analytes under controlled laboratory conditions, but also under environmental conditions. As shown, the 10-based monolayer has also been used to detect $Cr^{6+}$ in environmental samples. Water from a fishing pond and playground sand samples were collected and analyzed with and without the addition of ppm-levels of $Cr^{6+}$. The $Cr^{6+}$ was extracted from the sand with water. All water samples were acidified to pH=1. Only contaminated samples gave positive responses.

In view of the aforesaid, in one embodiment, the optical properties of the $Os^{2+}$-, $Fe^{2+}$- or $Ru^{2+}$-based pyridyl complex are optical absorption spectra of said pyridyl complex at the UV/visible spectral range, preferably at the range of 400-900 nm.

In another embodiment, the $Cr^{6+}$ sensor device of the present invention comprises a divalent $Os^{2+}$-based pyridyl complex, wherein said device is further capable of changing its oxidation state in response to a reduction of $Fe^{3+}$ at neutral pH, for detection of $Fe^{3+}$.

The $Cr^{6+}$ sensor device of the present invention may further comprise a substrate carrying a layered structure of the $Os^{2+}$-, $Fe^{2+}$- or $Ru^{2+}$-based pyridyl complex as defined above.

In one embodiment, the layered structure of the $Os^{2+}$-, $Fe^{2+}$- or $Ru^{2+}$-based pyridyl complex comprises a monolayer of said pyridyl complex.

In another embodiment, the layered structure of the $Os^{2+}$-, $Fe^{2+}$- or $Ru^{2+}$-based pyridyl complex comprises a plurality of identical or different layers of said pyridyl complex.

In a further embodiment, (i) the pyridyl complex is bound to a linker designed to covalently bind to the surface of said substrate; or (ii) the surface of said substrate carries a functional group capable of coordinating or binding to said layered structure. In a preferred embodiment, the functional group is capable of either covalently or non-covalently binding to said layered structure. The linker may be, without being limited to, a saturated or unsaturated, substituted or unsubstituted alkylene; a saturated or unsaturated, substituted or unsubstituted alkylaryl group; or a saturated or unsaturated, substituted or unsubstituted heterocycloalkyl groups, wherein said linker is attached to a functional group. Non-limiting examples of functional groups, when attached either to the linker or to the surface of the substrate, include silanes, thiols, phosphonates and alkenes.

In yet a further embodiment, the substrate is hydrophilic, hydrophobic or a combination thereof.

In one embodiment, the substrate includes a material selected from glass, a doped glass, indium tin oxide (ITO)-coated glass, silicon, a doped silicon, Si(100), Si(111), $SiO_2$, SiH, silicon carbide mirror, quartz, a metal, metal oxide, a mixture of metal and metal oxide, group IV elements, mica, a polymer such as polyacrylamide and polystyrene, a plastic, a zeolite, a clay, wood, a membrane, an optical fiber, a ceramic, a metalized ceramic, an alumina, an electrically-conductive material, a semiconductor, steel or a stainless steel. In preferred embodiments, the substrate as defined hereinabove is in the form of beads, microparticles, nanoparticles, quantum dots or nanotubes.

In one embodiment, the substrate is optically transparent to the UV and visible spectral ranges.

In a most preferred embodiment, the $Cr^{6+}$ sensor device of the present invention comprises a substrate carrying a layered structure of an $Os^{2+}$-based pyridyl complex as defined above, wherein said substrate is glass, more preferably glass slides or beads, said pyridyl complex is the compound of the general formula I wherein M is Os, n is 2, m is 1, X is $PF_6^-$ or $I^-$, $R_5$, $R_7$ to $R_{26}$ and $R_{28}$ each is hydrogen, $R_6$ is methyl, and $R_{27}$ is A, wherein $R_4$ is C≡C, $R_3$ is N, $R_2$ is propyl, and $R_1$ is trimethoxysilane (compounds 10a or 10b, respectively), and a monolayer of said pyridyl complex is covalently bound to said substrate.

In another aspect, the present invention relates to an acidic aqueous solution comprising a divalent osmium ($Os^{2+}$)-, iron ($Fe^{2+}$)- or ruthenium ($Ru^{2+}$)-based pyridyl complex capable of changing its oxidation state in response to a reduction of $Cr^{6+}$ at the presence of $H^+$, for selective detection and quantification of $Cr^{6+}$.

The pyridyl complex comprised within the acidic aqueous solution of the present invention may be any $Os^{2+}$-, $Fe^{2+}$- or $Ru^{2+}$-based pyridyl complex as defined above such as, without being limited to, any one of compounds 4-15.

In one embodiment, the solution of the present invention comprises $Os^{2+}$-based pyridyl complex as defined above. In a preferred embodiment, the solution has a pH at the range of 0.1-3, preferably 0.3-2, most preferably about 1.

In a further aspect, the present invention relates to an ampoule containing an acidic aqueous solution as defined above.

In yet a further aspect, the present invention relates to a kit containing at least two ampoules as defined above.

In still another aspect, the present invention provides a method for selective detection and quantification of $Cr^{6+}$ in a liquid sample, comprising:
(i) exposing a divalent osmium ($Os^{2+}$)-, iron ($Fe^{2+}$)- or ruthenium ($Ru^{2+}$)-based pyridyl complex capable of changing its oxidation state in response to a reduction of $Cr^{6+}$ to said sample, for a sufficient time period at the presence of $H^+$;
(ii) recording absorption spectra of said pyridyl complex at the UV/visible spectral range, preferably at the range of 400-900 nm; and
(iii) monitoring the presence of $Cr^{6+}$ in said sample and determining its concentration according to the change in the absorption spectra of (ii) compared to a predetermined absorption spectra of said pyridyl complex.

The pyridyl complex used according to this method may be any $Os^{2+}$-, $Fe^{2+}$- or $Ru^{2+}$-based pyridyl complex as defined above such as, without being limited to, any one of compounds 4-15.

In another embodiment, the pyridyl complex used according to this method is carried as a layered structure on a substrate as defined above.

In one embodiment, the liquid sample analyzed according to this method is obtained as a result of treating a solid sample by a liquid media.

In one embodiment, the pyridyl complex used according to this method is $Os^{2+}$-based pyridyl complex as defined above. In a preferred embodiment, a decrease of the metal to ligand charge transfer (MLCT) bands at λ=516 and 692 nm indicates the presence of $Cr^{6+}$, and the percentage of said decrease is proportional to the concentration of $Cr^{6+}$ in said sample. In another preferred embodiment, the $Os^{2+}$-based pyridyl complex is exposed to the sample analyzed at a pH in a range of 0.1-3, preferably 0.3-2, most preferably about 1, and the $Os^{2+}$-based pyridyl complex is exposed to the sample analyzed for about 1 min.

As shown in the Examples section hereinafter, the $Cr^{6+}$ detection method is redox coupled, i.e., associated with the oxidation of the 10-based monolayer from $Os^{2+}$ to $Os^{3+}$, followed by $Cr^{3+}$ generation; and the oxidation of the Os metal center may be reversibly switched in solution, depending of the pH, with subsequent $Cr^{3+}$ formation. In view of that, a chemically surface bound 10-based monolayer may effectively be applied in a reactor for $Cr^{6+}$ waste water treatment, i.e., for $Cr^{6+}$ detoxification. As particularly shown in Example 9, the $Cr^{6+}$ detoxification process is, in fact, a catalytic process, in which $Cr^{6+}$ is reduced with $Os^{2+}$-based pyridyl complex to thereby oxidize the $Os^{2+}$ to $Os^{3+}$, and the $Os^{3+}$ is then exposed to water, to thereby regenerate the $Os^{3+}$ to $Os^{2+}$.

Thus, in yet another aspect, the present invention provides a method for detoxification of $Cr^{6+}$ in an aqueous or organic liquid media, comprising:

(i) contacting said liquid media with a divalent osmium ($Os^{2+}$)-, iron ($Fe^{2+}$)- or ruthenium ($Ru^{2+}$)-based pyridyl complex capable of changing its oxidation state to $Os^{3+}$-, $Fe^{3+}$- or $Ru^{3+}$-based pyridyl complex, respectively, in response to a reduction of $Cr^{6+}$, for a sufficient time period at the presence of $H^+$, wherein said pyridyl complex is carried as a layered structure on a substrate;

(ii) monitoring the presence of $Cr^{6+}$ and determining its concentration in a sample taken from said liquid media; and (iii) when $Cr^{6+}$ is detected in said sample, reducing said $Os^{3+}$-, $Fe^{3+}$- or $Ru^{3+}$-based pyridyl complex and repeating steps (i) and (ii).

The pyridyl complex used according to this method may be any $Os^{2+}$-, $Fe^{2+}$- or $Ru^{2+}$-based pyridyl complex as defined above such as, without being limited to, any one of compounds 4-15.

In one embodiment, the substrate is in the form of beads, nanoparticles, quantum dots or nanotubes.

The monitoring of the presence of $Cr^{6+}$ and the determination of its concentration in step (ii) of this method may be carried out by any suitable method known in the art, e.g., by flame atomic absorption spectrometry (FAAS), inductively coupled plasma atomic emission spectrometry (ICP-AES), chemiluminescence, X-ray fluorescence, electrochemical methods or by the method for selective detection and quantification of $Cr^{6+}$ in a liquid sample as defined above.

In one embodiment, the pyridyl complex used according to this method is $Os^{2+}$-based pyridyl complex as defined above. In a preferred embodiment, the $Os^{2+}$-based pyridyl complex is contacted with the sample treated at a pH in a range of 0.1-3, preferably 0.3-2, most preferably about 1.

In yet a further aspect, the present invention provides a method for detoxification of $Cr^{6+}$ in an aqueous or organic liquid media, comprising contacting said liquid media with a divalent osmium ($Os^{2+}$)-, iron ($Fe^{2+}$)- or ruthenium ($Ru^{2+}$)-based pyridyl complex capable of changing its oxidation state to $Os^{3+}$, $Fe^{3+}$ or $Ru^{3+}$-based pyridyl complex, respectively, in response to a reduction of $Cr^{6+}$, for a sufficient time period at the presence of $H^+$, wherein said pyridyl complex is carried as a layered structure on a substrate.

In still a further aspect, the present invention provides a catalytic process for reduction of $Cr^{+6}$, comprising reducing said $Cr^{6+}$ with a divalent osmium ($Os^{2+}$)-based pyridyl complex to thereby oxidize the $Os^{2+}$ to $Os^{3+}$, and exposing the oxidized $Os^{3+}$ to water for a sufficient time period to thereby regenerate the $Os^{3+}$ to $Os^{2+}$.

The invention will now be illustrated by the following non-limiting Examples.

EXAMPLES

Materials and Methods

General. Most metal salts were purchased from BDH or Merck. $MgCl_2$ was purchased from Aldrich. All chemicals where used as received. Solvents (Reagent Grade) were purchased from Bio-Lab (Jerusalem), Frutarom (Haifa) or Mallinckrodt Baker (Phillipsburg, N.J.). [Os(bpy)$_3$]Cl$_2$ was prepared by a modification of the procedure described by Johnson et al. (1988) with $NH_4OsCl_6$, ethylene glycol, while purification was done by precipitation with $Et_2O$. The monolayers were synthesized and characterized as previously reported (Gupta et al., 2006). Soda-Lime glass used for monolayer preparation was cleaned by washing several times with deionised (DI) water, followed by immersion in a piranha solution (7:3 (v:v) $H_2SO_4$:30% $H_2O_2$) for 1 h (Caution: piranha is an extremely dangerous oxidizing agent thus should be carefully handled using appropriate personal protection). The glass substrates were again cleaned after the piranha treatment with DI water and placed in RCA (1:5:1 (v:v:v) $NH_4OH$:$H_2O$:30% $H_2O_2$) for 1 h. Subsequently, the substrates were rinsed with isopropanol, dried under $N_2$ flow and oven dried for 2 h. UV/visible spectra were recorded at room temperature, unless stated otherwise, on a Cary 100 spectrophotometer in transmission mode (260-900 nm). The functionalised glass substrates were fixed in a Teflon holder (1.5×0.75 cm window) and an identical glass substrate without monolayer was used to compensate for the background absorption.

Optical detection of $Cr^{6+}$ in solution. A stock solution of 1000 ppm $K_2Cr_2O_7$ in MeCN was prepared by dissolving 16 mg $K_2Cr_2O_7$ in 1 ml water whereafter 19 ml MeCN was added. This solution was diluted twice and acidified with 60 µl 32% HCl, and the UV/visible spectrum was recorded using MeCN as a background. The same was done with a MeCN solution of compound 10. After both spectra were taken, the two solutions were mixed together and the UV/visible spectrum was immediately recorded with a $K_2Cr_2O_7$ solution as the background reference.

Time-dependent oxidation of the 10-based monolayer by $Cr^{6+}$. A stock solution of 1000 ppm $K_2Cr_2O_7$ in MeCN was prepared as described above. The 10-based monolayer was immersed in an acidified MeCN (pH 1) 0.5 ppm $K_2Cr_2O_7$ solution for 2, 4, 6-16 min. The glass substrate was dried at room temperature and gently wiped with task paper and the UV/visible spectrum was then recorded.

pH dependence of $Cr^{6+}$ detection. 100 ppm $K_2Cr_2O_7$ solutions in DI water at a pH ranging from 7 to 0 were prepared by adding a specified amount of 1M HCl to the $K_2Cr_2O_7$ solutions, with increments of 0.5 pH units between pH 0-3, and with increments of 1 pH unit between pH 3-7. The 10-based monolayer was immersed in the various solutions for 1 min, subsequently dried and gently wiped with task paper, and the UV/visible spectra were then recorded. After each experiment, the 10-based monolayer was reset as described above. Removal of the monolayer from the glass substrates was observed by UV/visible spectroscopy at pH>9.

Selective sensing of $Cr^{6+}$ in aqueous matrices. A stock solution of 1000 ppm of $K_2Cr_2O_7$ in DI water was prepared by dissolving 20 mg $K_2Cr_2O_7$ in 20 ml water. Stock solutions of each one of the metal salts used were prepared by dissolving $5 \times 10^{-4}$ mol of the corresponding metal salt in 100 ml DI water. A typical experiment was carried out as follows: The aqueous metal salt solution (1 ml) was further diluted with 8 ml DI water, and 100 µl of 32% HCl was then added. The 10-based monolayer was immersed in the obtained solution for 1 min and after drying, the UV/visible spectrum was recorded. Then, 1 ml of the $K_2Cr_2O_7$ stock solution was added to the same aqueous metal salt solution, the monolayer was again immersed for 1 min, and the UV/visible spectrum was recorded.

Effect of $Fe^{3+}$ on the oxidation of the sensor by $Cr^{6+}$. Aqueous solutions at pH 1 were prepared, containing 80 ppm of $FeCl_3$ or $K_2Cr_2O_7$. The 10-based monolayer was immersed for 5 min in a $FeCl_3$ solution and the UV/visible spectrum was recorded with 1 min time intervals. The same was done with the $Cr^{6+}$ solution, only for a 3 min time window, since saturation of the sensor was already achieved after 1 min exposure time. The same $FeCl_3$ sample was made basic, pH 14, while after $Fe^{3+}$ precipitated as its hydroxide. The solution was filtered using 2 µm pore Teflon filter, and the filtrate was reacidified to pH 1. The 10-based monolayer was then immersed again for 5 min, during which the UV/visible spectrum was recorded with 1 min time intervals.

Environmental detection of $Cr^{6+}$. (a) A water sample was collected from a pond located at the campus of the Weizmann Institute of Science (Rehovot, Israel) and divided into two fractions of 10 and 9 ml respectively. One ml of 1000 ppm $K_2Cr_2O_7$ was added to the latter sample, and both samples were acidified with 100 μl 32% HCl. The 10-based monolayer was immersed in both samples for 1 min, and their UV/visible spectra were then recorded. The same was done with $K_2Cr_2O_7$ concentrations of 5 and 10 ppm respectively, with 2 min immersion time. (b) A 100 g sand sample was collected from a playground located at the campus of the Weizmann Institute of Science and divided into two portions of 20 g each, and 10 mg $K_2Cr_2O_7$ was then added to one of the portions. 100 ml DI water were added to both portions and then vigorously stirred for 2 h under heating (60° C.). Both solutions were then filtered, and 10 ml of the filtrates were collected. After cooling to room temperature, 100 μl 32% HCl was added to each one of the collected filtrates, and the 10-based monolayer was immersed for 1 min in both solutions. Then, the substrate was dried and gently wiped with task paper and the UV/visible spectrum was recorded.

pH dependence of the $H_2O$ oxidation. Water samples with different pH values ranging between 1-7.5, with increments of 1 pH unit, as well as a 50 ppm aqueous solution of $K_2Cr_2O_7$ at pH 1 were prepared. The 10-based monolayer was fully oxidized by immersion for 3 min in the 50 ppm aqueous $K_2Cr_2O_7$ solution and subsequently washed for 1 min in dry MeCN, and the UV/visible spectrum was then recorded to confirm full oxidation of the 10-based monolayer. When fully oxidized, the monolayer was immersed for 3 min in water at pH 1. The glass substrate was then dried and gently wiped with task paper and the UV/visible spectrum was recorded. This procedure was repeated for all the water samples at different pH values, and was further used when the 10-based monolayer was oxidized with a 100 ppm $NOBF_4$ solution in dry MeCN.

Detection of $Cr^{3+}$ by electron spin resonance (ESR). A 10 ml 6 mM aqueous solution of $[Os(bpy)_3]Cl_2$ at pH 1, and a 10 ml 2 mM aqueous solution of $K_2Cr_2O_7$ at pH 1 were prepared. Subsequently, 2 ml of both solutions were mixed together, and a gradual color change was observed from dark green to red/purple. Directly after mixing, the ESR spectrum of the mixed solution was recorded.

Example 1

Preparation of the $Os^{2+}$-Based Pyridyl Complex 10

In order to prepare the $Os^{2+}$-based pyridyl complex 10, compound 3 was first synthesized starting from compound 1, using a modified literature procedure (Kim and Shin, 2003), and the preparation of compound 10 from compound 3 was performed in two steps as previously described (Gupta et al., 2006). As particularly depicted in Scheme 1 hereinafter, the preparation of compound 10 included the following steps:

(i) Synthesis of 4'-methyl-4-(2-(4-pyridyl)ethan-2-ol)-2,2'-bipyridine, 2. A solution of 4,4'-dimethyl-2,2'-bipyridine, 1 (2.2 g, 11.9 mmol), in tetrahydrofuran (THF, 50 ml) was prepared under Argon, and freshly prepared lithiumdiisopropylamine (LDA) (8 ml, 12.6 mmol, BuLi and 1.6 ml, 12.7 mmol diisopropylamine in 16 ml THF) was added to the solution while stirring during 30 min at 0° C. After 1 h of additional stirring, 4-pyridinecarboxy aldehyde (1.2 ml, 12.8 mmol) in 10 ml THF was added dropwise, and the solution was allowed to stir overnight whereupon the color changed from green to orange. The reaction was quenched with water and the THF was evaporated under reduced pressure. The remaining solution was extracted (3×100 ml) with $CH_2Cl_2$, and the organic layer was then washed with saturated NaCl and dried with $Na_2SO_4$. Thereafter, the solvent was removed under reduced pressure and the residue was purified using column chromatography (150 g neutral alumina G-II). The eluent was changed from $CH_2Cl_2$ to 2% MeOH in $CH_2Cl_2$ as the starting material was identified on thin layer chromatography (TLC), yielding 1.3 g, 25%, compound 2 as a light yellow/orange solid, as identify by TLC (2% MeOH in $CH_2Cl_2$).

(ii) Synthesis of 4'-methyl-4-(2-(4-pyridyl)ethynyl)-2,2'-bipyridine, 3. Compound 2 (2.9 g, 9.9 mmol) was dried for 0.5 h under vacuum, and dry pyridine (24 ml) was then added under Argon. Using schlenk techniques, a solution of $POCl_3$ (3.9 ml, 41.8 mmol) in dry pyridine (16 ml) was prepared and added dropwise during 30 min at room temperature, to the solution of compound 2, and the solution was allowed to stir for at least additional 1 h. The pyridine was carefully removed under vacuum and the residue was dissolved in water. The pH of the aqueous solution was adjusted to pH 7-8 with a concentrated NaOH solution, and the solution was extracted (3×100 ml $CH_2Cl_2$). The organic layers were combined, washed with saturated NaCl and dried with $Na_2SO_4$. The solvent was removed under reduced pressure and the residue was purified using column chromatography (150 g neutral alumina G-II) while gradually increasing the solvent polarity from $CH_2Cl_2$ to 2% MeOH in $CH_2Cl_2$, yielding 0.65 g (50%) of compound 3 as a light yellow solid. The structure and purity of compound 3 was verified by TLC (2% MeOH in $CH_2Cl_2$) and $^1H$ NMR spectroscopy.

(iii) Preparation of bis(2,2'-bipyridine)[4'-methyl-4-(2-(4-pyridyl)ethenyl)-2,2'-bipyridine]osmium(II)[bis(hexaflaorophosphate)/di-iodide], 4. $Os(bpy)_2Cl_2 \cdot 2H_2O$ (200 mg, 0.328 mmol) was reacted with compound 3 (107 mg, 0.39 mmol) under reflux in 50 ml ethanol-water (1:1, v:v) for 24 h to provide a dark green solution, which was concentrated to ~10 ml under vacuum. Compound 4 was precipitated by addition of an excess of a saturated $NH_4PF_6$ solution in water (150 mg in 3 ml). The precipitate was washed with an excess of water (100 ml) and afterwards with diethylether (50 ml), and was then purified by column chromatography (neutral alumina, G-III) using toluene/MeCN (8:2 v:v) as eluent. The second green fraction was collected and dried under vacuum to afford compound 4 (yield: 220 mg, 63%). The structure and purity of compound 4 was verified by $^1H$ and $^{13}C$ NMR spectroscopy and mass spectroscopy.

(iv) Preparation of bis(2,2'-bipyridine)[4'-methyl-4-(2-(4-(3-propyl trim ethoxysilane)pyridinium)ethenyl)-2,2'-bipyridine]osmium(II)[tris (hexafluorophosphate)/tri-iodide], 10. 3-iodopropyltrimethoxy silane (67 mg, 0.23 mmol) in excess was added to a dry THF/MeCN (9:1 v:v) solution (20 ml) of compound 4 (50 mg, 0.047 mmol) under $N_2$ in a pressure vessel. The reaction mixture was stirred at 90° C. for 72 h and the volume was then reduced to ~2 ml. The addition of dry pentane (15 ml) resulted in the precipitation of compound 10 at room temperature. The solvent was decanted and washed with dry pentane (3×60 ml) under vacuum to afford compound 10 (yield: 56 mg, 88%). The structure and purity of compound 10 was verified by $^1H$ and $^{13}C$ NMR spectroscopy and mass spectroscopy.

Importantly, when the concentrations of compound 2 and phosphoroxychloride where increased, considerable better yields, i.e., 50-75%, were obtained.

Scheme 1. Preparation of the Os²⁺-based pyridyl comlex 10

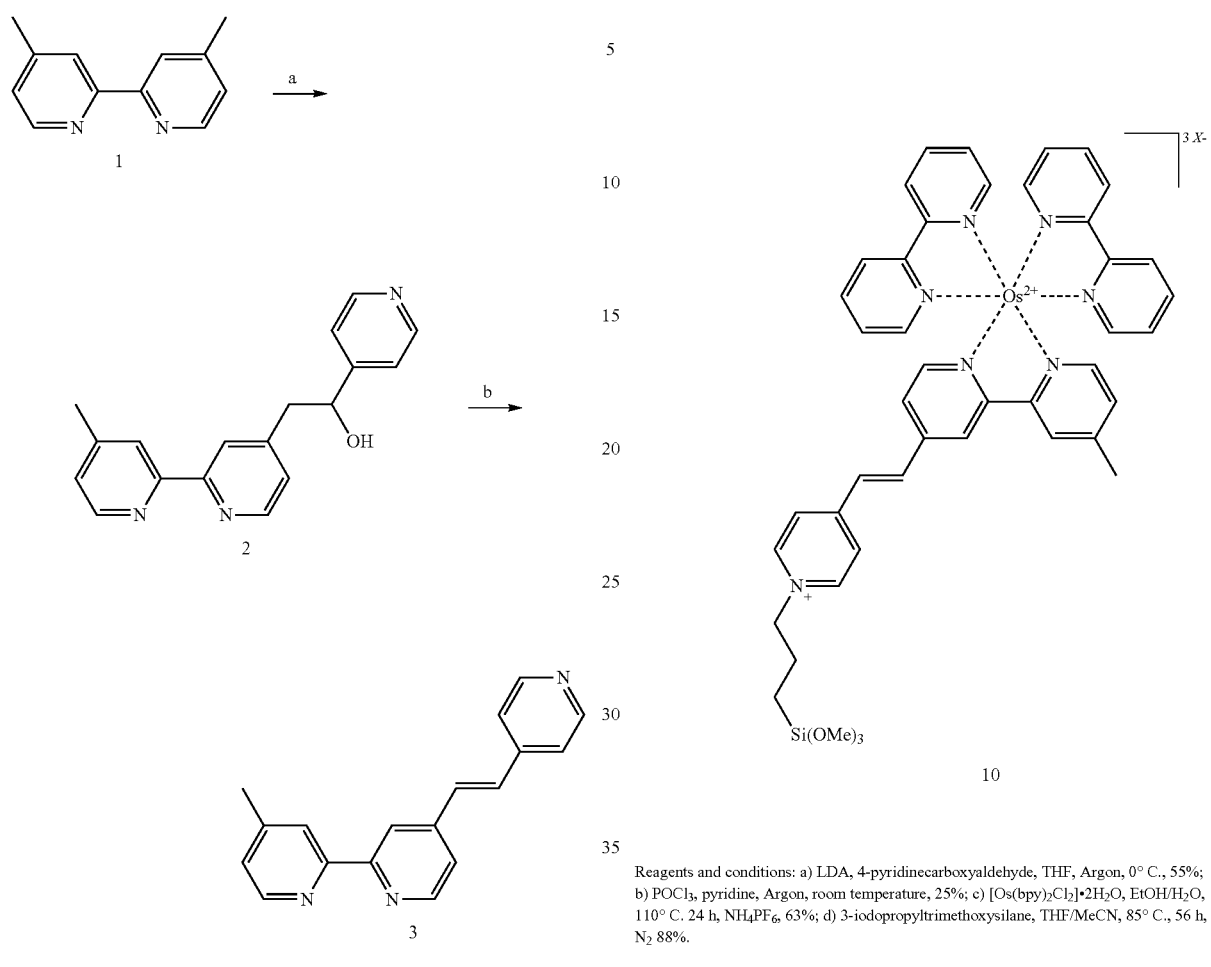

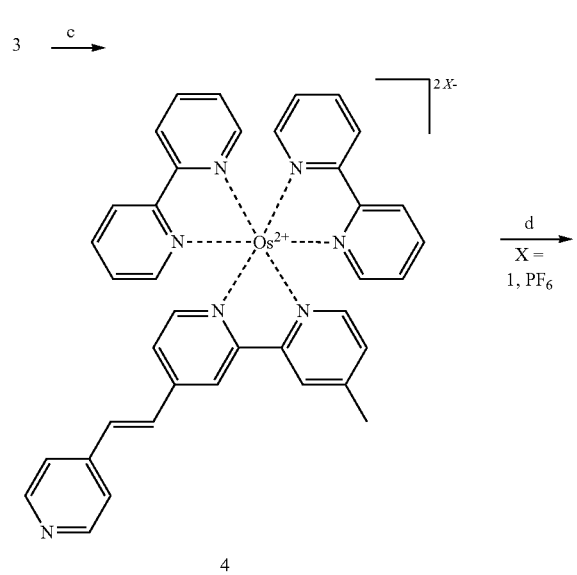

Reagents and conditions: a) LDA, 4-pyridinecarboxyaldehyde, THF, Argon, 0° C., 55%; b) POCl₃, pyridine, Argon, room temperature, 25%; c) [Os(bpy)₂Cl₂]·2H₂O, EtOH/H₂O, 110° C. 24 h, NH₄PF₆, 63%; d) 3-iodopropyltrimethoxysilane, THF/MeCN, 85° C., 56 h, N₂ 88%.

Example 2

Formation of Compound 10-Based Monolayers on Glass

Monolayers of compound 10 on glass were formed as previously described and are illustrated in Scheme 2 hereinafter. In particular, freshly cleaned glass substrates (0.1×0.8×2.5 cm) were loaded under $N_2$ atmosphere into a pressure tube that contained a 0.5 mM solution of compound 10 in acetonitrile/toluene (3:7 v:v). The pressure tube was sealed and allowed to react for 52 h at 85° C., and the functionalized substrates were then rinsed with acetonitrile under $N_2$ atmosphere and sonicated for 8 mM each in acetonitrile, acetone and isopropanol. The samples were dried under $N_2$ flow and stored in the dark.

Scheme 2. Illustration of compound 10-based monolayer on glass

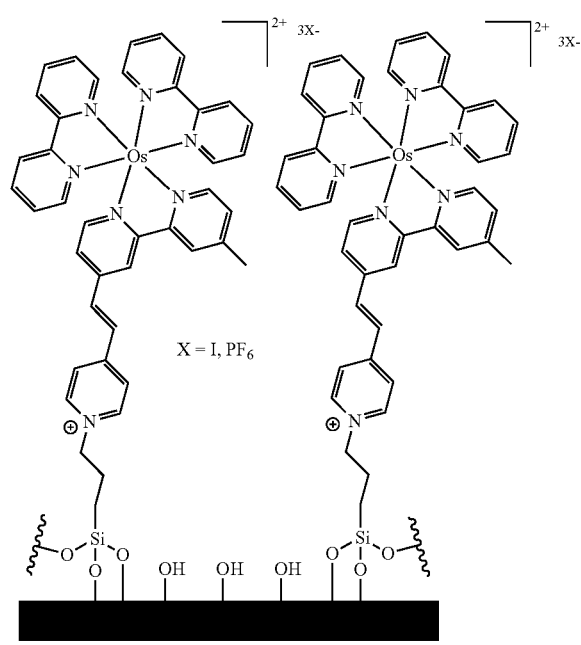

X = I, PF$_6$

These monolayers are robust and have previously been characterized with atomic force microscopy (AFM) and UV/visible spectroscopy (Gupta et al., 2006). As has further been shown (Gupta et al., 2006, 2007; Gupta and van der Boom, 2006, 2007; Gulino et al., 2007), the UV/visible spectrum of the 10-based monolayer shows characteristic metal-to-ligand charge-transfer (MLCT) bands at λ=692 and 516 nm respectively, which can be addressed by changing the metal oxidation state of the d$^6$ metal centre. For instance, oxidation of Os$^{2+}$ to Os$^{3+}$ induces the bleaching of the MLCT bands with a subsequent increase of the ligand-to-metal charge-transfer (LMCT) band at λ=317 nm. This has previously been exploited to detect H$_2$O, NO$^+$ in organic solvents, Fe$^{3+}$ in organic and aqueous media, and NO$_x$ in the gasphase.

Example 3

Cr$^{6+}$ Oxidizes Compound 10

Since Cr$^{6+}$ undergoes reduction in solution in the presence of H$^+$ and low-valent metal centers such as Fe$^{2+}$, Mn$^{2+}$ and V$^{3+}$, it was speculated that such a reaction would also be possible between Os$^{2+}$ and Cr$^{6+}$. For this reaction, acidic conditions are required as it is well known that K$_2$Cr$_2$O$_7$ is a strong oxidizing agent only under acidic conditions (E°=+1.33 V), whereas under basic conditions it is a poor oxidizer (E°=−0.13 V). Indeed, reaction of compound 10 (20.8 μM) in MeCN with an excess (1.7 mM) of K$_2$Cr$_2$O$_7$ in MeCN, at pH 1, resulted in electron transfer from the osmium metal center to the Cr$^{6+}$ metal center, as indicated by the characteristic bleaching of the MLCT bands at λ=516 and 692 nm and the increase of the LMCT band at λ=312 nm, and shown in FIG. 1. The electron transfer was also confirmed by electron spin resonance (ESR) that showed the formation of Cr$^{3+}$ by reacting a 6 mM aqueous solution of [Os(bpy)$_3$]Cl$_2$ with 2 mM aqueous solution of K$_2$Cr$_2$O$_7$ at pH 1.

Example 4

Compound 10 Optically Recognizes ppm Levels of Cr$^{6+}$

Figure 2:
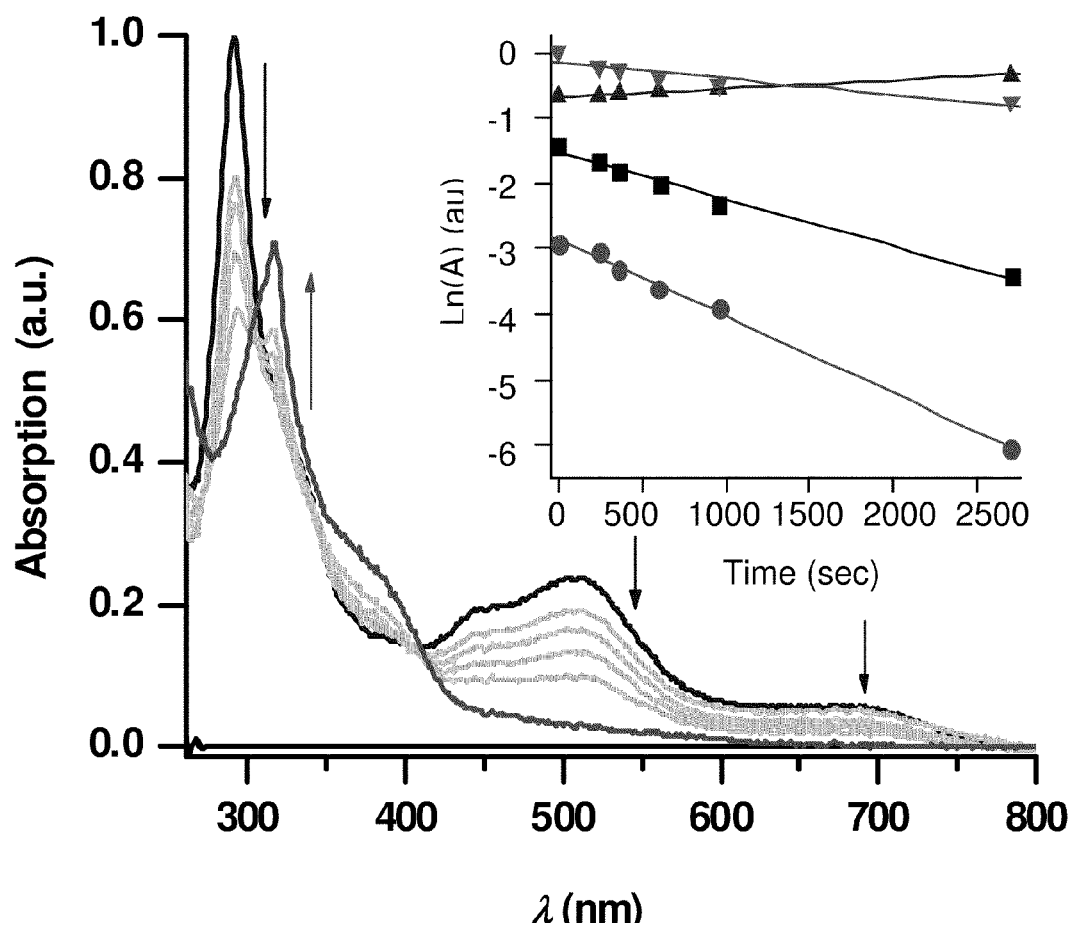
FIG. 2 shows absorption changes of the 10-based monolayer immersed in an acidified MeCN solution (pH=1) containing 0.5 ppm $Cr^{6+}$. The inset shows the absorption changes at λ=516 (■) $R^2$=0.990, λ=692 nm (●) $R^2$=0.997, λ=317 nm (▲) $R^2$=0.979, and λ=293 nm (▼) $R^2$=0.850, at 4, 6, 10, 16, and 45 min, respectively.

As found in a series of experiments, using K$_2$Cr$_2$O$_7$ as the Cr$^{6+}$ source, trace amounts of Cr$^{6+}$ in aqueous or organic solution can be detected in situ by monitoring the optical properties of the 10-based monolayer by UV/visible spectroscopy in the transmission mode (260-800 nm). In particular, immersing a 10-based monolayer on glass (0.8×2.5×0.1 cm) in an acidified MeCN solution containing 0.5 ppm Cr$^{6+}$ resulted in a significant decrease of the absorption band at λ=293 nm and both singlet and triplet states of metal-to-ligand charge-transfer (MLCT) bands at λ=516 and 692 nm, and a concurrent increase of the ligand-to-metal charge-transfer (LMCT) band at λ=317 nm, as shown in FIG. 2. As further shown in FIG. 2 (inset), saturation of the sensor occurred under these reaction conditions after 45 minutes. The 10-based monolayer was stable in H$_2$O at pH=1 for at least several hours in the absence of Cr$^{6+}$, as indicated by UV/visible spectroscopy.

Figure 3:
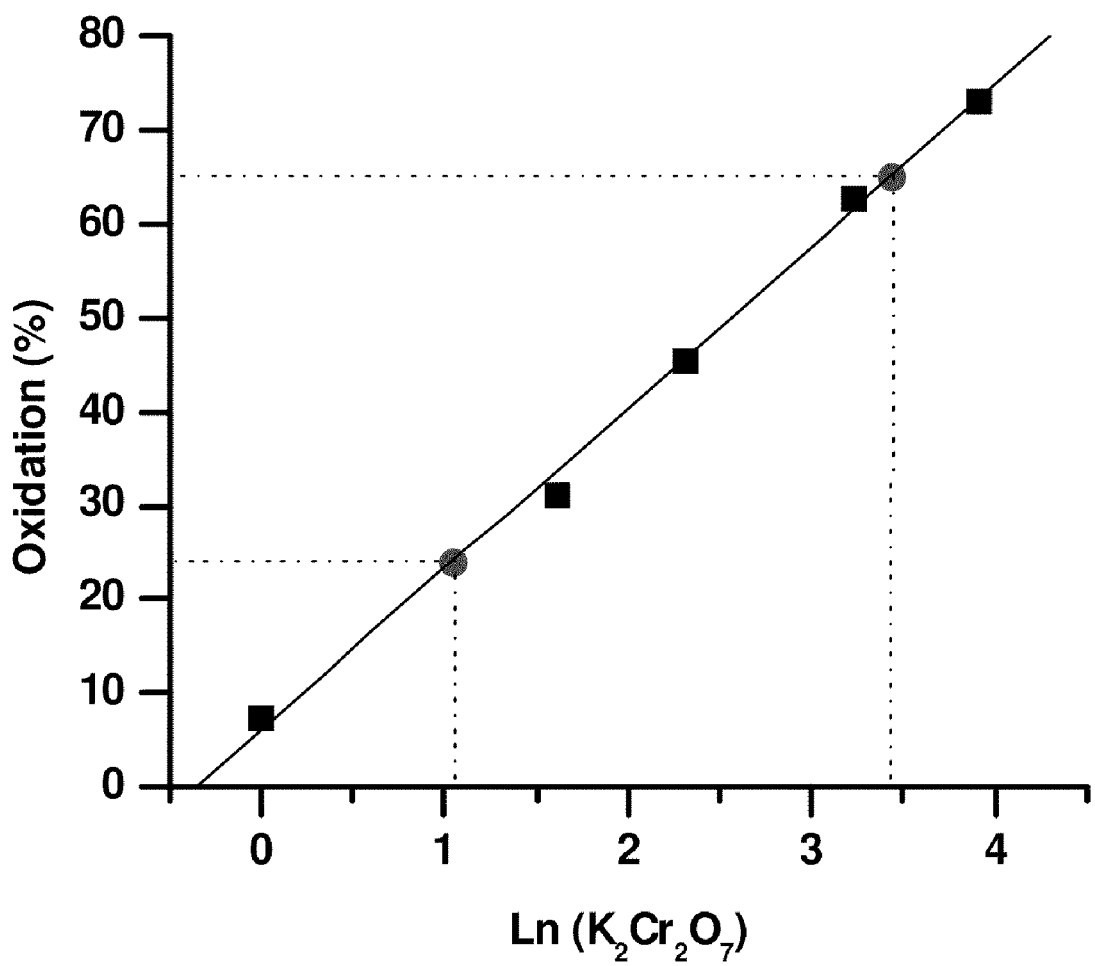
FIG. 3 shows the absorption changes in oxidation % after a 1-min exposure of the 10-based monolayer to aqueous solutions containing 0, 1, 5 10, 25 or 50 ppm $Cr^{6+}$ at pH=1. The black line represents a linear fit ($R^2$=0.996). The dots show the results of a blind test, performed with standard acidic (pH 1) aqueous solutions containing 3 and 28 ppm of $Cr^{6+}$.
Figure 4:
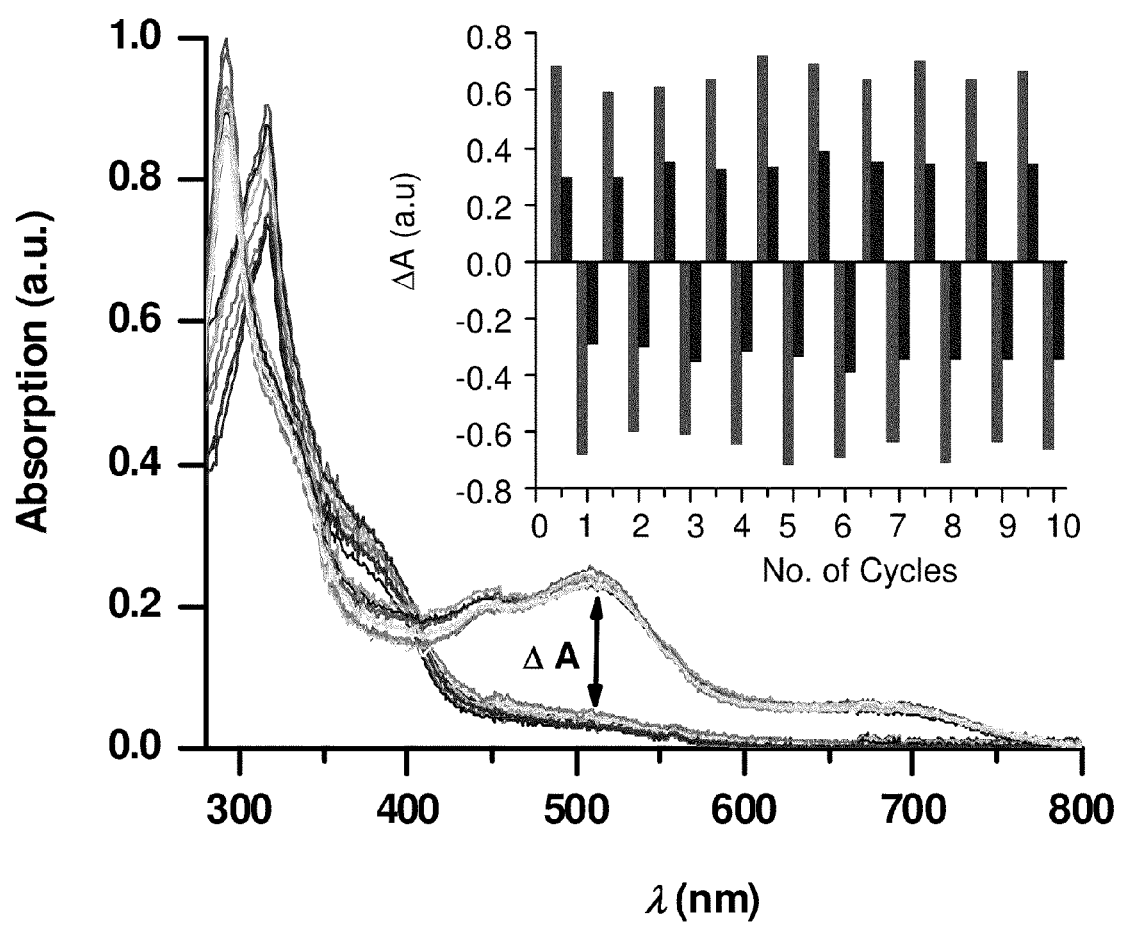
FIG. 4 shows absorption spectra of a typical switching experiment where the 10-based monolayer was oxidized for 1-min with an acidified MeCN solution (pH<1) containing 5 ppm $Cr^{6+}$, and subsequently reduced with $H_2O$ within 3-min. the inset shows the spectral changes of the MLCT bands at λ=516 and 692 nm (long and short bars, respectively), as a function of the oxidation/reduction cycles.

In order to evaluate its Cr$^{6+}$ sensing quality, the 10-based monolayer was immersed for 1 min in aqueous (pH 1) solutions containing various concentrations (0, 1, 5, 10, 25 or 50 ppm) of K$_2$Cr$_2$O$_7$, where after subsequently their UV/visible absorption spectra were recorded, and a representative calibration curve of the 10-based monolayer with these solutions is shown in FIG. 3. The good linear correlation and the system stability allowed reliable and accurate quantification of Cr$^{6+}$, and was further verified by performing a blind test with standard acidic (pH 1) aqueous solutions containing 3 and 28 ppm of Cr$^{6+}$. As particularly shown in FIG. 3, the blind test showed that even after several weeks in air, the calibrated 10-based sensor could be used to determine the amount of Cr$^{6+}$ within 10% accuracy. The detection range in H$_2$O and MeCN was 1-100 ppm and 0.5-100 ppm, respectively. Reduction of the Os$^{3+}$ system by water completely restores the MLCT bands at λ=516 and 692 nm to their original values, as shown in FIG. 4 (Gupta and van der Boom, 2006, 2007; Gupta et al., 2006; For water-mediated reduction of Ru$^{3+}$ and Os$^{3+}$ complexes in solution, see: Zong and Thummel, 2005; Hurst, 2005; Lay and Sasse, 1985).

Example 5

Catalytic Properties of the 10-Based Monolayer

In this experiment, the effect of consecutive oxidation/reduction cycles on the 10-based monolayer, i.e., its oxidation/reduction reversibility, was examined. In particular, the 10-based monolayer sensor was immersed in a 5 ppm K$_2$Cr$_2$O$_7$ solution in acidic MeCN (pH 1) for 1 min, whereafter; it was reset by immersing for 1 min in MeCN, quick washing with basic water (pH~8) and then immersing again in water for 3 min. After each oxidation/reduction cycle, the substrates were subsequently dried and gently wiped with task paper and the UV/visible spectrum was recorded. These cycles were repeated up to 10 times to show complete reversibility. As shown in FIG. 4, the surface-solution redox chemistry is dependent on the pH and shows good reversibility for at least 10 redox cycles. The complete reversibility of the of the 10-based monolayer is particularly shown in the inset of this figure, wherein negative values correspond to the "oxidative" bleaching of the MLCT bands and positive values correspond to the "reductive" restoration of these bands, indicating that every oxidation/reduction cycle caused about the same change, ΔA, for the oxidation and the reduction process.

Figure 5:
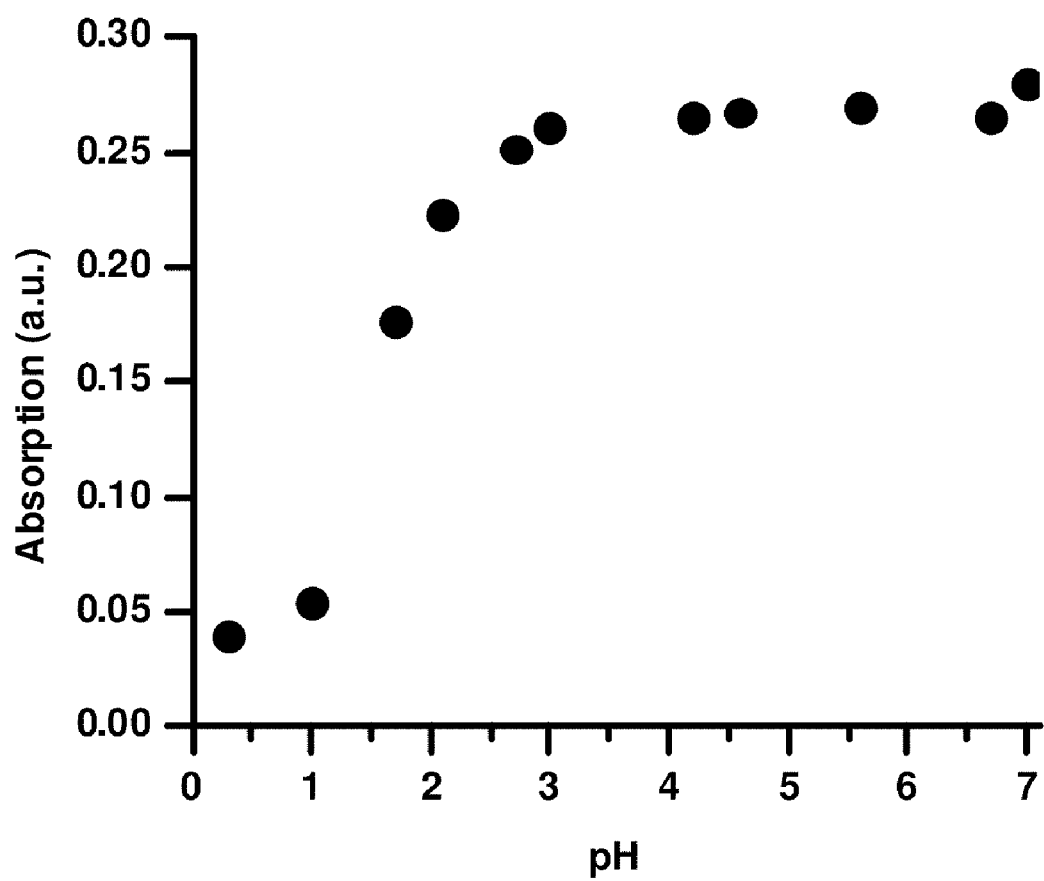
FIG. 5 shows absorption of the 10-based monolayer at λ=516 nm after immersion for 1-min in an aqueous solution containing 100 ppm $Cr^{6+}$ at different pH values.

Ex situ UV/visible follow-up experiments, as described in Materials and Methods, demonstrated that the system responds to the analyte only at a pH<3 for a 1-min exposure time, as shown in FIG. 5. The highest oxidation rate was observed at pH=0.3. Interestingly, reduction of the sensor with $H_2O$ was pH dependent as well. The maximum reduction rate was observed at pH=7.5, whereas at pH=1, hardly any reaction is observed. The monolayer setup became unstable at higher pH values, which is common for siloxane-based monolayers (Wasserman et al., 1989).

Figure 6A:
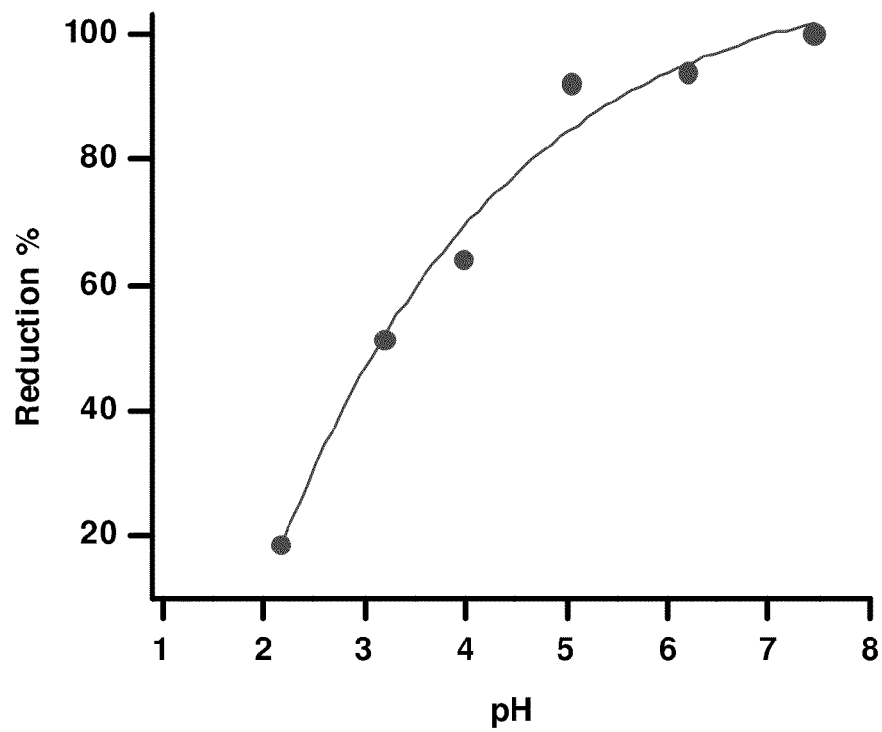
FIGS. 6A-6B show the optical response of the 10-based monolayer, expressed in reduction percentage, as a function of the pH. The pH dependent reduction of the 10-based monolayer with $H_2O$, wherein oxidation was performed with 50 ppm $K_2Cr_2O_7$ ($R^2$=0.983) (6A); and the pH dependent reduction of the 10-based monolayer with $H_2O$, wherein oxidation was performed with 100 ppm $NOBF_4$ in MeCN ($R^2$=0.996) (6B).
Figure 6B:
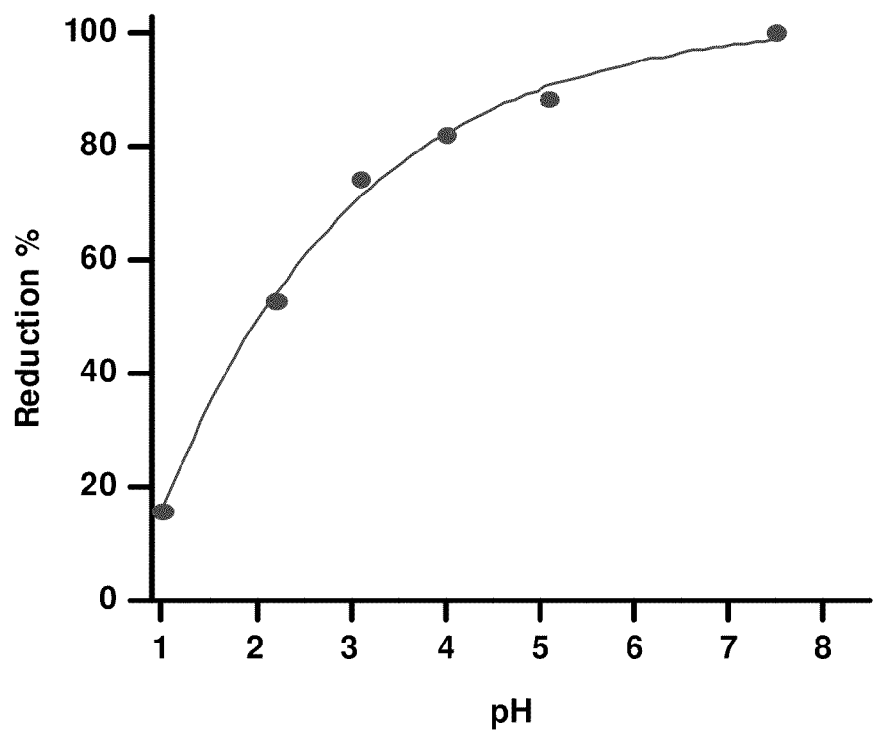
Figure 7A:
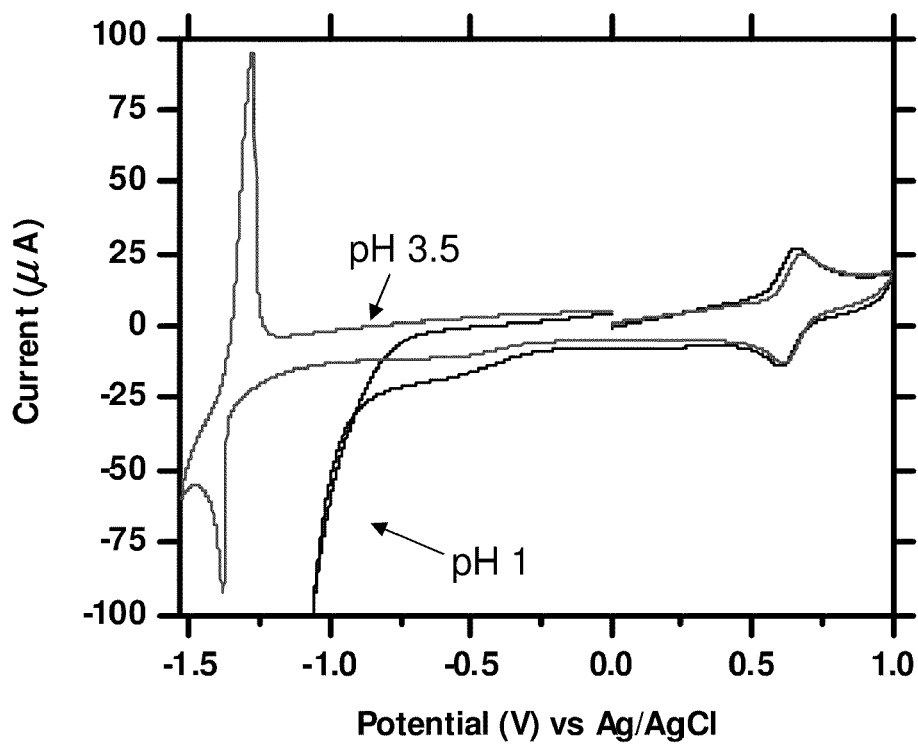
FIGS. 7A-7B show cyclic voltammogram for $[Os(bpy)_3]Cl_2$, in 0.1 M KCl solution in water at a scan rate of 100 mV/s between −1.6 and +1.0 V, with a glassy carbon working electrode and a Pt-wire counter electrode with Ag/AgCl as reference, at pH 3.5 and pH 1 (7A); and cyclic voltammogram for $[Os(bpy)_3]Cl_2$, in 0.1 M KCl solution in water at a scan rate of 400 mV/s, isolating the Os-metal center between 0 and 1 V, at pH 3.5 and pH 1 (7B).
Figure 7B:
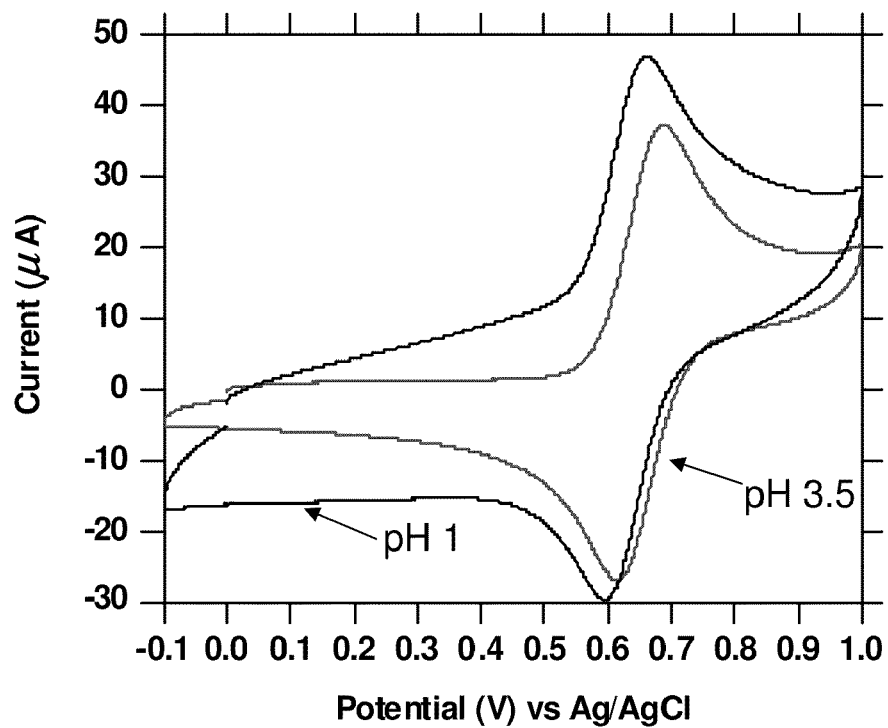

The pH dependence of the water oxidation of the 10-based monolayer was evaluated as described in Materials and Methods, and the optical response of the 10-based monolayer, expressed in reduction % as a function of pH, is shown in FIGS. 6A-6B. As particularly found, the recovery of the 10-based monolayer at low pH values was rather difficult, in contrast to neutral pH values where 100% recovery was observed, suggesting that the pH might have an interesting effect on the electrode potential of the used 10-based monolayer. Therefore, $[Os(bpy)_3]Cl_2$, closely resembles the confined osmium-complex on glass, was chosen, and its cyclic voltammograms in 0.1 M KCl solution) are shown in FIGS. 7A-7B.

Figure 8A:
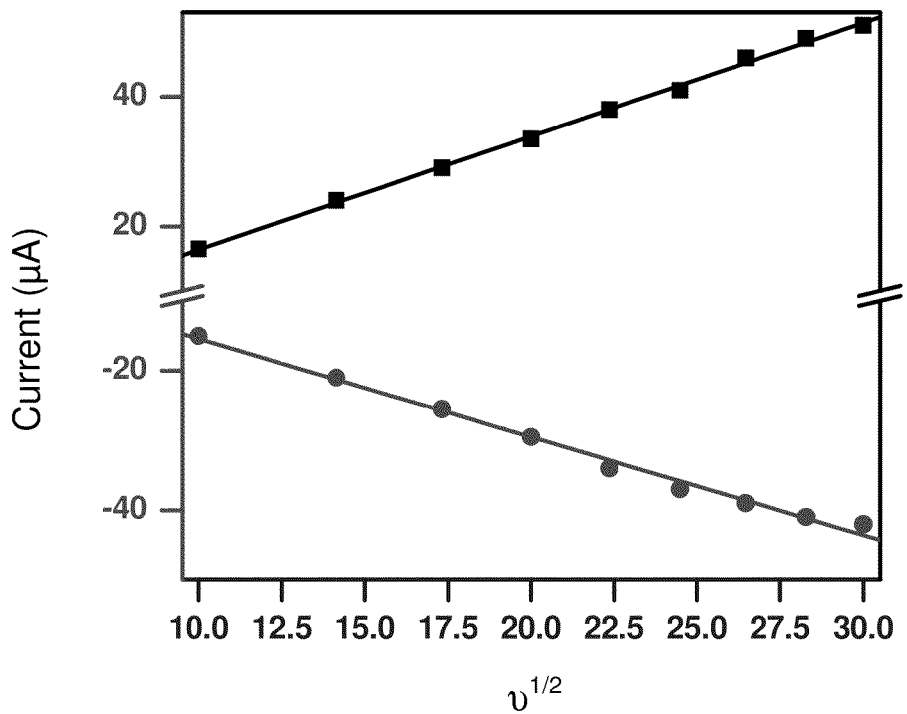
FIGS. 8A-8B show a plot of $I_p$ vs. $v^{1/2}$ for $[Os(bpy)_3]Cl_2$ at pH 1 (8A) and pH 3.5 (8B), representing a linear correlation indicating a diffusion controlled oxidation/reduction process.
Figure 8B:
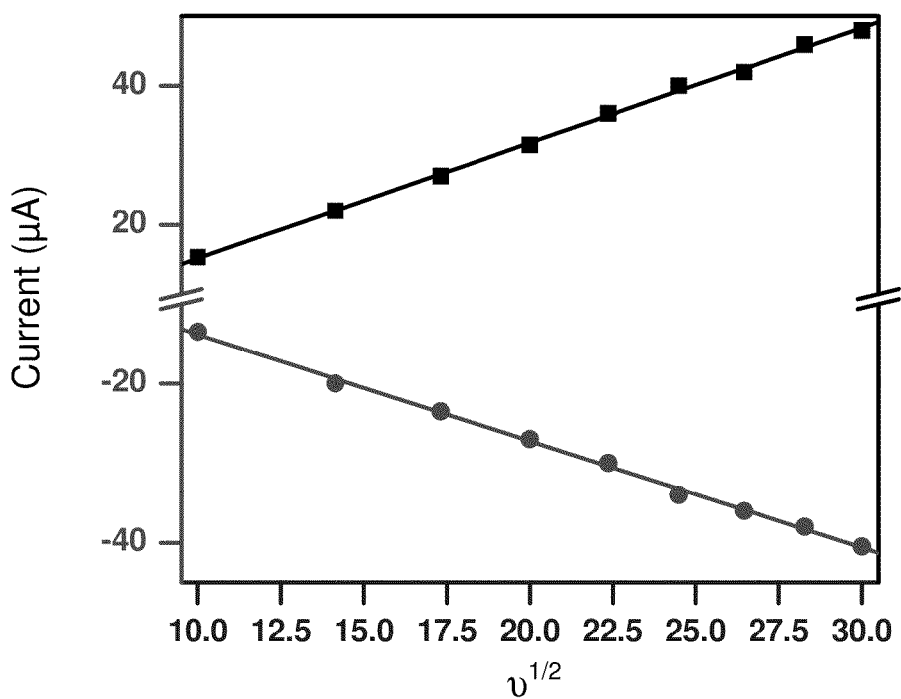

In water, the first oxidation process at E=0.61 V is associated with the oxidation of $Os^{2+}$ to $Os^{3+}$. This process is reversible and indicated by a peak separation of 60 mV and a linear correlation between $I_p$ and $v^{1/2}$, characteristic for reversible processes (FIGS. 8A-8B). As shown in FIG. 7B, there was no significant effect of the pH on the redox potential of the Os-metal center, i.e., the oxidation/reduction potentials were only shifted 20 mV upon acidification from pH 3.5 to 1, while increasing the pH from 3.5 to 12 did not lead to any change in the cyclic voltammogram. In water, however, only one irreversible oxidation peak was observed for the bipyridine ligand around −1.3 V, instead of two oxidation processes observed in MeCN (Matsumurainoue et al., 1986). In view of that it is suggested that the pH has no effect on the redox potential of $[Os(bpy)_3]Cl_2$, thus the pH dependence must be caused by a mechanistic effect.

Example 6

Compound 10 is Highly Selective to $Cr^{6+}$ in the Presence of $H^+$

Figure 9:
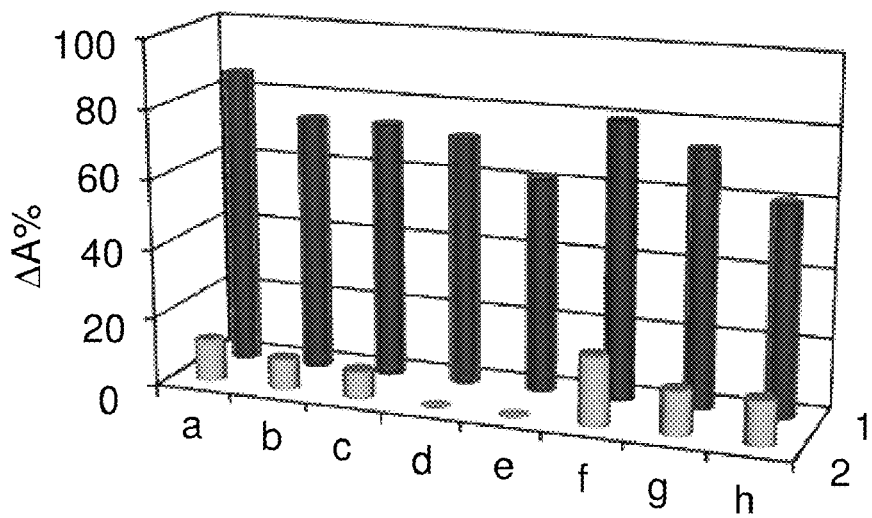
FIG. 9 shows relative oxidation change of the 10-based monolayer at λ=516 nm, after immersion in various aqueous matrices containing $5 \times 10^{-4}$ M of each of the following metals salts, with (row 1) and without (row 2) the presence of 100 ppm $Cr^{6+}$. a) $HgCl_2$, $ZnCl_2$, $CuCl_2$, $CoCl_2$, $MnCl_2$ and $NiCl_2$; b) $MgCl_2$, $BaCl_2$ and $CaCl_2$; c) KCl, NaCl, CsCl and LiCl; d) $LaCl_3$, $Al(NO_3)_3$ and $CdSO_4$; e) $NaNO_3$, $Na_2SO_4$, $Na_2SO_3$, $KH_2PO_4$ and KBr; f) $Pb(NO_3)_2$ and $NaNO_2$; g) $FeCl_3$; and h) $FeCl_3$ after sample treatment with a strong base to selectively remove $Fe^{3+}$.

In order to test the selectivity of the 10-based monolayer towards $Cr^{6+}$, a series of aqueous solutions containing various metal ions, e.g., alkali, alkaline earth and transition metal ions, or anions commonly found in groundwater (Förstner and Wittman, 1981) were prepared as described in Materials and Methods, and the relative oxidation change of the 10-based monolayer at λ=516 nm, after immersion in each one of these solutions, with and without the presence of $Cr^{6+}$, was tested. The specific solutions prepared and used in this experiment consisted of (a) $HgCl_2$, $ZnCl_2$, $CuCl_2$, $CoCl_2$, $MnCl_2$ and $NiCl_2$; (b) $MgCl_2$, $BaCl_2$ and $CaCl_2$; (c) KCl, NaCl, CsCl and LiCl; (d) $LaCl_3$, $Al(NO_3)_3$ and $CdSO_4$; (e) $NaNO_3$, $Na_2SO_4$, $Na_2SO_3$, $KH_2PO_4$ and KBr; (f) $Pb(NO_3)_2$ and $NaNO_2$; (g) $FeCl_3$; and (h) $FeCl_3$ (after sample treatment with a strong base to selectively remove $Fe^{3+}$). As shown in FIG. 9, only samples containing $Cr^{6+}$ induced significant optical changes (ΔA≧60%) after a 1-min exposure time. Furthermore, the selectivity of $Cr^{6+}$ over $Fe^{3+}$ was remarkable.

Figure 10:
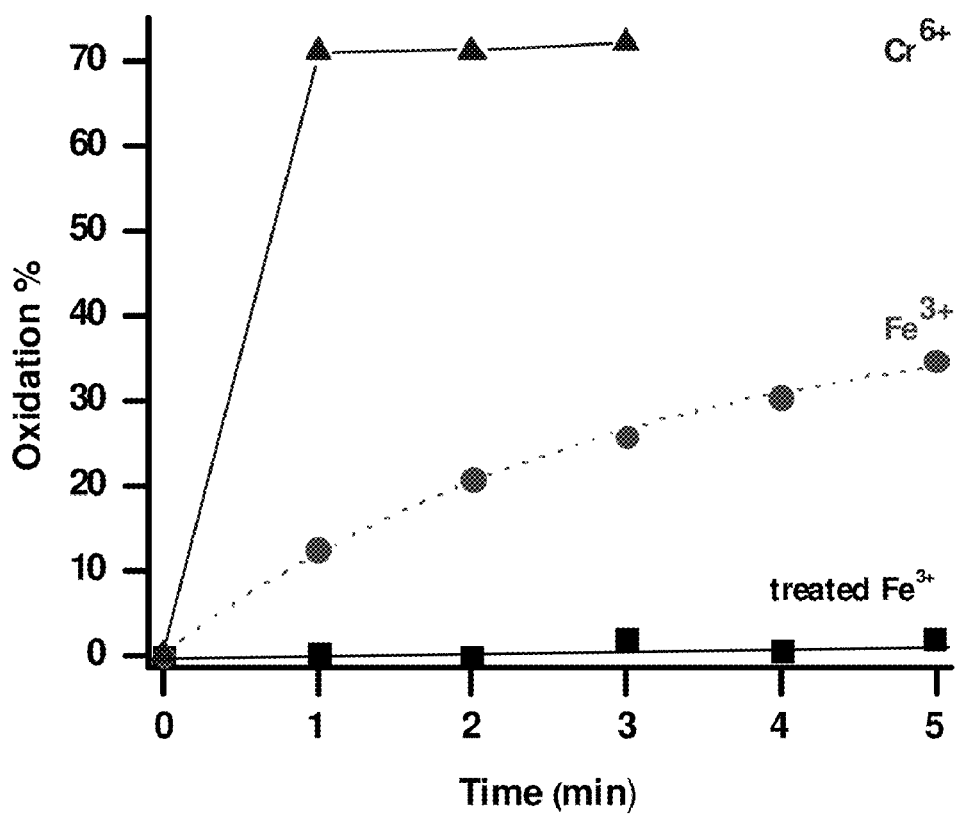
FIG. 10 shows the absorption changes at λ=516 nm of the 10-based monolayer as a function of time upon immersion in aqueous solutions (pH 1) containing 80 ppm $Cr^{6+}$ (■) and $Fe^{3+}$ (●; $R^2$=0.998). The line represented by the character ■ represents the absorption of the 10-based monolayer after treatment with a strong base to selectively remove $Fe^{3+}$, as described in Materials and Methods.

Whereas the 10-based sensor did not respond to $Cr^{6+}$ in the absence of $H^+$, as shown above, it was capable of optically sensing $Fe^{3+}$ in $H_2O$ and MeCN, under neutral conditions, as we have previously described (Gupta and van der Boom, 2007). Apparently, this dual sensor system was capable of detecting a specific metal ion by varying the pH. Time-dependent measurement of the oxidation of the 10-based monolayer by aqueous solutions containing 80 ppm $Fe^{3+}$ or $Cr^{6+}$ showed that the optical response of the sensor towards the latter ion was at least 6 times greater within 1-min of exposure time, as shown in FIG. 10. Moreover, $Fe^{3+}$ could selectively be removed from the medium by treatment with a strong base, as described in Materials and Methods, prior to analysis of the $Cr^{6+}$ content by the 10-based monolayer (FIG. 9, entry h). $Cr^{6+}$ is stable under basic conditions (Ji et al., 2001).

Example 7

Compound 10 Optically Recognizes $Cr^{6+}$ in Environmental Samples

Figure 11:
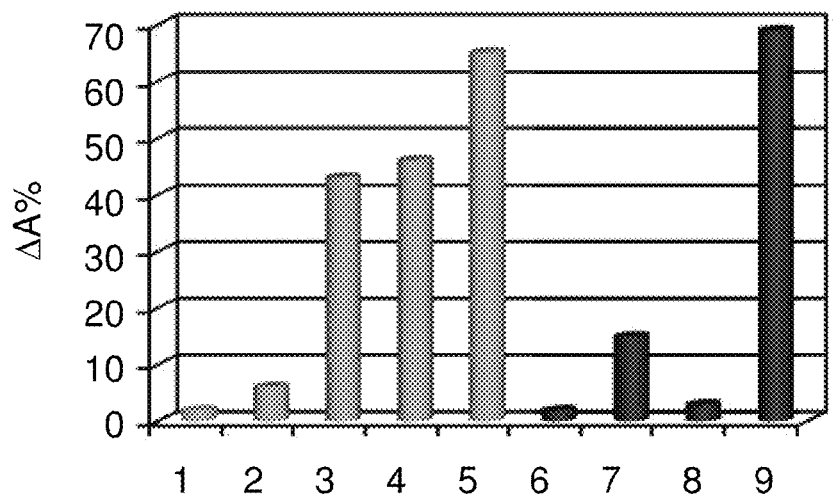
FIG. 11 shows optical response, expressed in oxidation %, of the 10-based monolayer at λ=516 nm after immersion for 1-min in pond water (entries 1-5) and sand-extracted water (entries 6-9) under acidic conditions (pH=1). Entries 1 and 2 represent pond water with and without acid added to the sample, respectively; entries 3 and 4 represent 5 and 10 ppm $Cr^{6+}$, respectively, with the same amount of acid, except for a 2-min response time; and entry 5 represents 100 ppm $Cr^{6+}$. Entries 6 and 7 represent water from the sand extraction, with and without acid added to the sample; and entries 8 and 9 represent samples that were taken from the sand+$Cr^{6+}$ extraction, in which the latter was acidified (pH=1).

The formation of device quality sensors requires not only the ability to detect analytes under controlled laboratory conditions, but also under environmental conditions. Indeed, the 10-based monolayer has also been used to detect $Cr^{6+}$ in environmental samples. Water from a fishing pond and playground sand samples were collected and analyzed with and without the addition of ppm-levels of $Cr^{6+}$, as described in Materials and Methods. The $Cr^{6+}$ was extracted from the sand with water. All water samples were acidified to pH=1. As shown in FIG. 11, only samples contaminated with $Cr^{6+}$ gave positive responses.

Example 8

The 10-Based Monolayer is Stable Under Acidic Conditions

Figure 12:
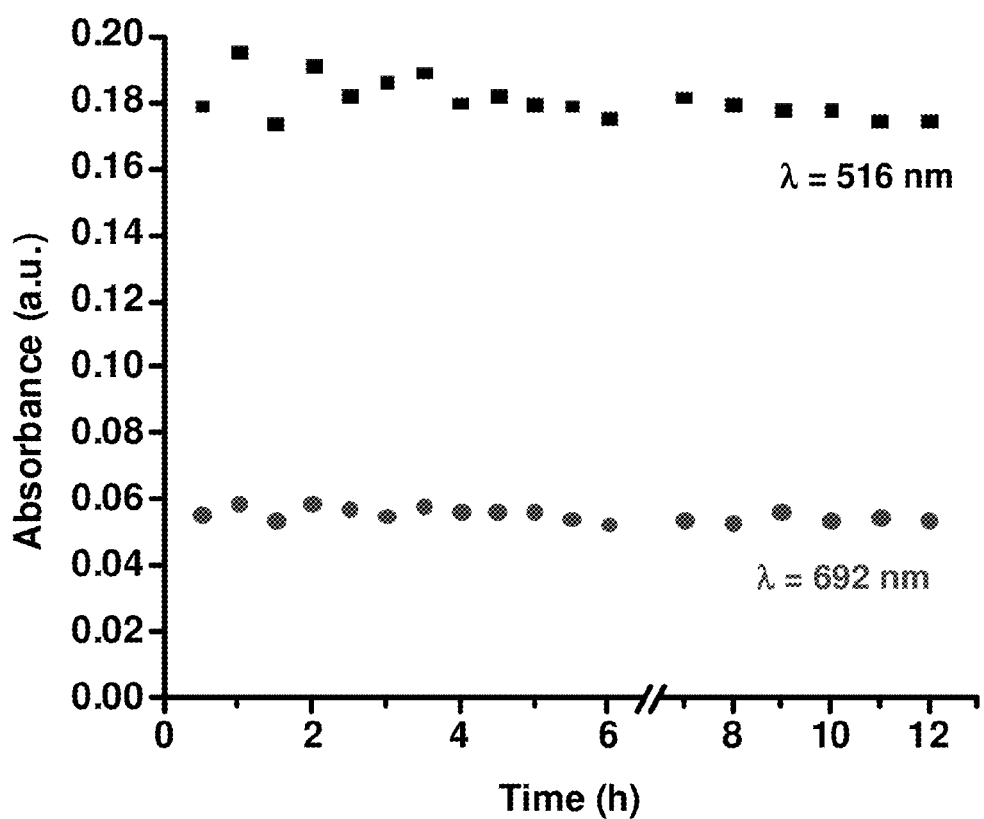
FIG. 12 shows the stability of both MLCT bands at λ=516 and 692 upon immersion the 10-based monolayer in acidic water (pH 1) for several hours. The break indicates a 16 h break, during which the 10-based monolayer was not immersed in the acidic water.

Since compound 10 was found to be highly selective to $Cr^{6+}$ in the presence of $H^+$ only, stability of the 10-based monolayer towards acidic conditions is preferable. In order to evaluate its stability under said conditions, the 10-based monolayer was immersed in water at pH 1 for several hours, the substrate was gently wiped with task paper and dried, and the absorption of MLCT bands at λ=516 and 692 were then recorded. As shown in FIG. 12, the 10-based monolayer was stable for at least 12 hours in an acidic environment; however, over a longer extended period of time (56 h), a decrease of 18% in the absorption of both MLCT bands was observed (data not shown). Nevertheless, comparing the stability at pH 1 for several hours with a 1 min response time of the 10-based monolayer in most experiments, it can be concluded that this monolayer is stable under conditions required for detection and quantification of $Cr^{6+}$. At high pH (>9), however, removal of the 10-based monolayer from the glass substrates was observed by hydrolysis of the Si—O bond, which is in good agreement with Wasserman et al. (1989).

Example 9

The 10-Based Monolayer may be Used for $Cr^{6+}$ Catalytic Detoxification

As shown in the preceeding Examples, the $Cr^{6+}$ detection method is redox coupled, i.e., associated with the oxidation of the 10-based monolayer from $Os^{2+}$ to $Os^{3+}$, followed by $Cr^{3+}$ generation as indicated by ESR. As was further shown, the oxidation of the Os metal center may be reversibly switched in solution, depending of the pH, as indicated by UV/visible spectra, with subsequent $Cr^{3+}$ formation.

Figure 13:
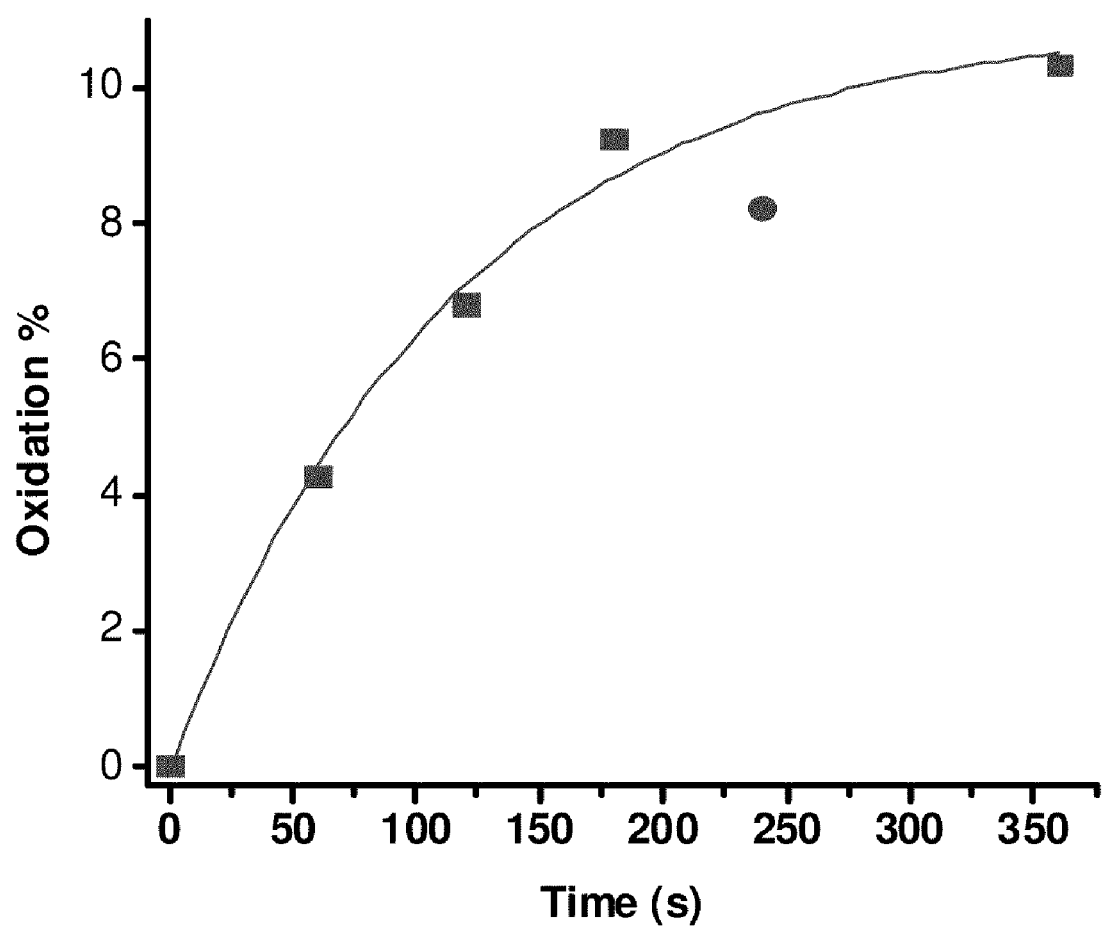
FIG. 13 shows the oxidation change in %, as a function of time, of the MLCT band at λ=516 nm of the 10-based monolayer after exposure to the solution, used in the experiment described in Example 9. The line shows an exponential fit with $R^2$=0.993.
Figure 14:
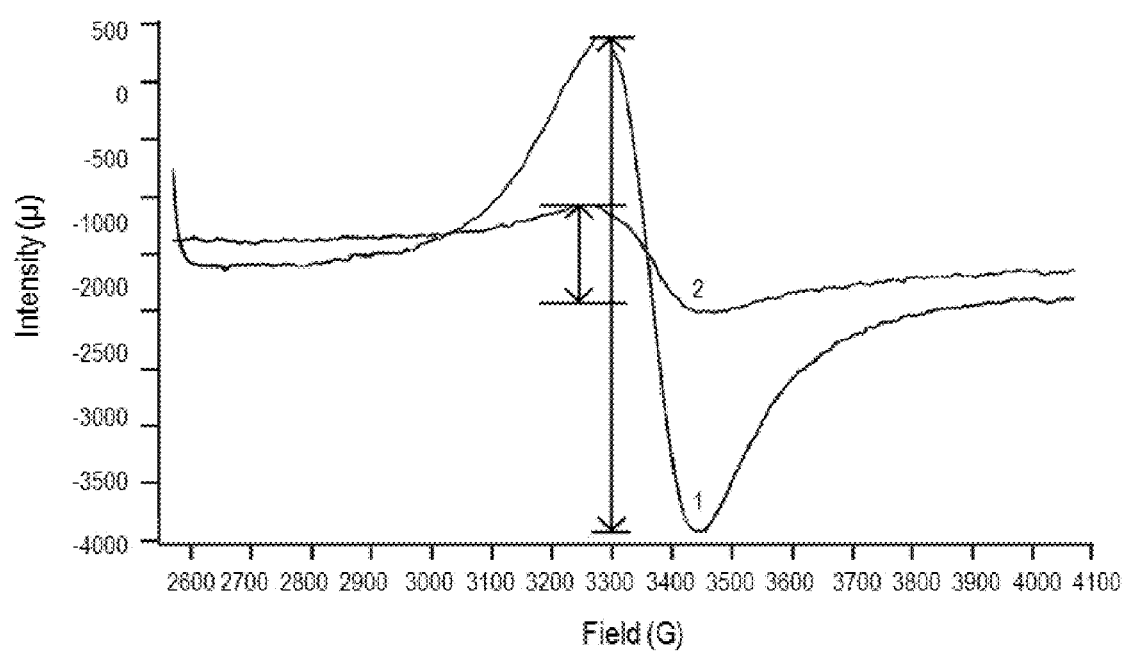
FIG. 14 shows electron spin resonance (ESR) spectrum of 2 mM solution of $CrCl_3$ in $H_2O$ at pH 1 (1); and a 1:1 (v:v) mixture of 2 mM $K_2Cr_2O_7$ and 6 mM $[Os(bpy)_3]Cl_2$ in $H_2O$ at pH 1 after 8 consecutive cycles, as described in Example 9 (2).
Figure 15:
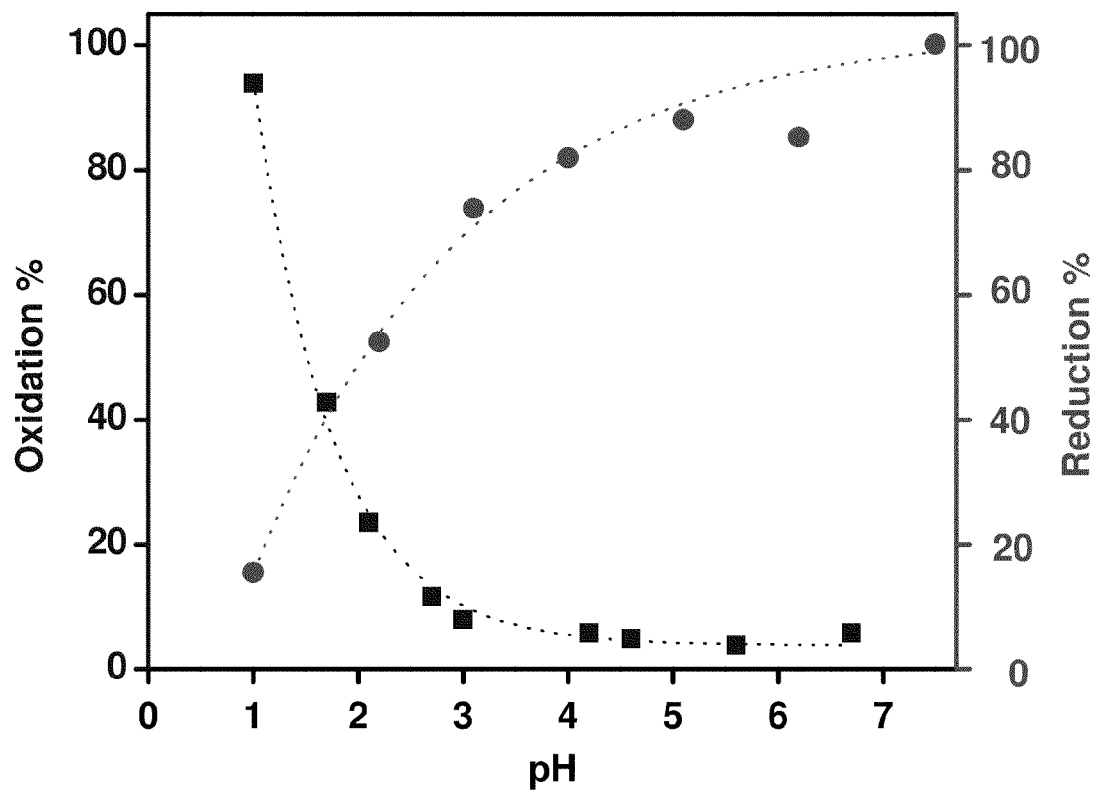
FIG. 15 shows changes of the oxidation (■) and reduction (♦) % of the MLCT at λ=516 nm of the 10-based monolayer as a function of the pH. Oxidation was done with 100 ppm $Cr^{6+}$ (red dots), whereas as the reduction was done with $H_2O$.

In a typical experiment, 1 mM $K_2Cr_2O_7$ (2 times excess) was reacted with 3 mM $[Os(bpy)_3]Cl_2$, and the pH of the obtained solution was modulated between pH 1-12, using 10 M HCl and 10 M KOH. After each addition of base/acid, the pH was measured and the solution was allowed to stir for additional 5 min. Upon acidification of the solution to pH 1, a fast color change was observed from dark green, indicating $Os^{2+}$, to red, indicating oxidation of the $Os^{2+}$ (as $Os^{3+}$ has no color, the red color was probably due to other interactions); however, when the solution was made basic, the reverse color change was observed from red to dark green (data not shown). These oxidation/reduction cycles were repeated (×8) until no color change was observed, and the final solution (pH 1) was analyzed for $Cr^{6+}$ using the 10-based monolayer. The monolayer was immersed for 6 min in the solution, at pH 1, during which the UV/visible spectrum was recorded with 1 min intervals, and as shown in FIG. 13, the amount of $Cr^{6+}$ detected by the 10-based monolayer after a 6 min exposure was ~>1 ppm (hence the 9% response of 1 ppm after 1 min) vs. 60 ppm in the original solution, indicating that switching of the oxidation state of the Os metal center may be done until the $Cr^{6+}$ amount is fully consumed. The solution was also analyzed by ESR for the presence of $Cr^{3+}$, and as shown in FIG. 14, $Cr^{3+}$ was indeed formed after the "catalytic" treatment of the initial 1 mM $K_2Cr_2O_7$ solution. FIG. 15 shows the oxidation of the 10-based monolayer by $Cr^{6+}$ and the resetting by $H_2O$, as a function of the pH, indicating that the optimum pH value for the catalytic reaction described above is probably between pH 1.5-3.0.

Figure 16:
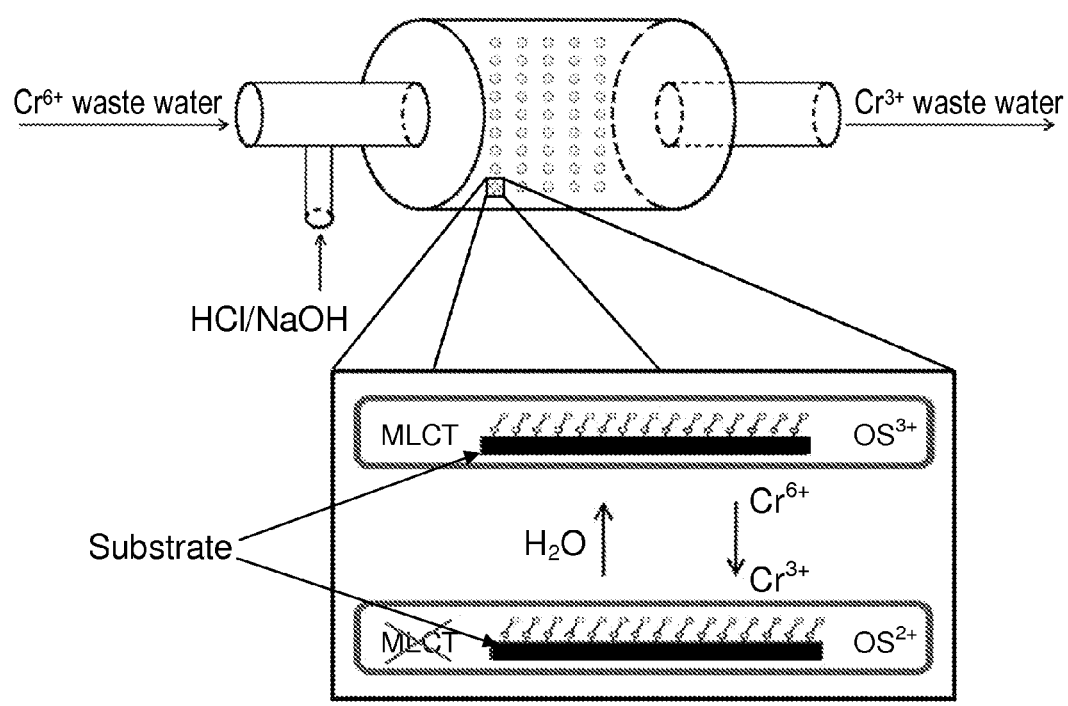
FIG. 16 shows a graphical representation of a potential reactor for catalytic detoxification of $Cr^{6+}$ waste water with glass beads functionalized with the 10-based monolayer. The magnification shows the probable surface processes.

In view of the experimental data described hereinabove, it is concluded that chemically surface bound 10-based monolayers may effectively be applied in a reactor for $Cr^{6+}$ waste water treatment. A graphical drawing of such a reactor, in which $Cr^{6+}$ waste water are catalytically detoxify with glass beads functionalized with 10-based monolayers, is shown in FIG. 16.

REFERENCES

Ashkenasy G., Ivanisevic A., Cohen R., Felder C. E., Cahen D., Ellis A. B., Shanzer A., *J. Am. Chem. Soc.*, 2000, 122, 1116
Baker B. R., Lai R. Y., Wood M. S., Doctor E. H., Heeger A. J., Plaxco K. W., *J. Am. Chem. Soc.*, 2006, 128, 3138
Basabe-Desmonts L., Beld J., Zimmerman R. S., Hernando J., Mela P., Garcia-Parajo M. F., Hulst N. F. van, Berg A. Van den, Reinhoudt D. N., Crego Calama M., *J. Am. Chem. Soc.*, 2004, 126, 7293
Birk J. P., *J. Am. Chem. Soc.*, 1969, 91, 3189
Boiadjiev V. I., Brown G. M., Pinnaduwage L. A., Goretzki G., Bonnesen P. V., Thundat T., *Langmuir*, 2005, 21, 1139
Collman J. P., Devaraj N. K., Decreau R. A., Yang Y., Yan Y. L., Ebina W., Eberspacher T. A., Chidsey C. E. D., *Science*, 2007, 315, 1565
Crooks R. M., Ricco, A. J., *Acc. Chem. Res.*, 1998, 31, 219
Davies K. M., Espenson J. H., *J. Am. Chem. Soc.*, 1970, 92, 1884
Eary L. E., Rai D., *Environ. Sci. Technol.*, 1988, 22, 972
EPA *Control and Treatment Technology for the Metal Finishing Industry: Sulfide Precipitation*, US Environmental Protection Agency, 1980
EPA *In Situ Treatment of Soil and Groundwater Contaminated with Chromium(VI)*, US Environmental Protection Agency, 2000
Espenson J. H., *J. Am. Chem. Soc.*, 1970, 92, 1880
Forstner V., Wittman G. T. W., *Metal Pollution in Aquatic Environment*; Springer-Verlag: Berlin, 1981
Fryxell G. E., Mattigod S. V., Lin, Y. H., Wu H., Fiskum S., Parker K., Zheng F., Yantasee W., Zemanian T. S., Addleman R. S., Liu J., Kemner K., Kelly S., Feng X. D., *J. Mater. Chem.*, 2007, 17, 2863
Gheju M., Iovi A., *J. Hazard Mater.*, 2006, 135, 66
Gulino A., Bazzano S., Condorelli G. G., Giuffrida S., Mineo P., Satriano C., Scamporrino E., Ventimiglia G., Vitalini D., Fragala I., *Chem. Mater.*, 2005, 17, 1079
Gulino A., Gupta T., Mineo P. G., van der Boom M. E., *Chem Commun.*, 2007, 4878
Gupta T., van der Boom M. E., *J. Am. Chem. Soc.*, 2006, 128, 8400
Gupta T., Altman M., Shukla A. D., Freeman D., Leitus G., van der Boom M. E., *Chem. Mater.*, 2006, 18, 1379
Gupta T., van der Boom M. E., *J. Am. Chem. Soc.*, 2007, 129, 12296
Gupta T., Cohen R., Evmenenko G., Dutta P., van der Boom M. E., *J. Phys. Chem. C*, 2007, 111, 4655
Hurst J. K., *Coord. Chem. Rev.*, 2005, 249, 313
Ji H. F., Thundat T., Dabestani R., Brown G. M., Britt P. F., Bonnesen P. V., *Anal. Chem.*, 2001, 73, 1572
Kieber R. J., Willey J. D., Zvalaren S. D., *Environ. Sci. Technol.*, 2002, 36, 5321
Kim D., Shin E. J., *Bull. Korean Chem. Soc.*, 2003, 24, 1490
Lahann J., Mitragotri S., Tran T., Kaido H., Sundaran J., Hoffer S., Somorjai G. A., Langer R., *Science*, 2003, 299, 371
Lay P. A., Sasse W. H. F., *Inorg. Chem.*, 1985, 24, 4707.
Levina A., Lay P. A., *Coord. Chem. Rev.*, 2005, 249, 281
Liu C. C., Wang M. K., Li Y. S., Lin Y. A., Chiou C. S., Huang S. S., *Ind. Eng. Chem. Res.*, 2006, 45, 8891
Liu Z., Yasseri A. A., Lindsey J. S., Bocian D. F., *Science*, 2003, 302, 1543
Marqués M. J., Salvador A., Morales-Rubio A. E., de la Guardia M., *Fresenius' J. Anal. Chem.*, 2000, 367, 601
Matsumurainoue T., Ikemoto I., Umezawa Y., *J. Electroanal. Chem.*, 1986, 209, 135
Mytych P., Stasicka Z., *Appl. Catal. B: Environ.*, 2004, 52, 167
Reynolds M., Stoddard L., Bespalov I., Zhitkovich A., *Nucl. Acids Res.*, 2007, 35, 465
Singh A. K., Gupta V. K., Gupta B., *Anal. Chim. Acta*, 2007, 585, 171
Tian F., Boiadjiev V. I., Pinnaduwage L. A., Brown G. M., Thundat T., *J. Vac. Sci. Technol. A*, 2005, 23, 1022
Turyan I., Mandler D., *Anal. Chem.*, 1997, 69, 894
Wasserman S. R., Tao Y. T., Whitesides G. M., *Langmuir*, 1989, 5, 1074
Westheimer F. H., *Chem. Rev.*, 1949, 45, 419
Yerushalmi R., Scherz A., van der Boom M. E., *J. Am. Chem. Soc.*, 2004, 126, 2700
Zhang S., Cardona C. M., Echegoyen L., *Chem Commun.*, 2006, 4461
Zhitkovich A., *Chem. Res. Toxicol.*, 2005, 18, 3
Zong R., Thummel R. P., *J. Am. Chem. Soc.*, 2005, 127, 12802

The invention claimed is:
1. A method for selective detection and quantification of $Cr^{6+}$ in a liquid sample, comprising:
(i) exposing a divalent osmium ($Os^{2+}$)-, iron ($Fe^{2+}$)- or ruthenium ($R^{2+}$)-based pyridyl complex capable of changing its oxidation state in response to a reduction of $Cr^{6+}$ to said sample, for a sufficient time period at the presence of $H^+$;

(ii) recording absorption spectra of said pyridyl complex at the UV/visible spectral range, and (iii) monitoring the presence of $Cr^{6+}$ in said sample and determining its concentration according to the change in the absorption spectra of (ii) compared to a predetermined absorption spectra of said pyridyl complex, wherein said pyridyl complex is a charged tris-bipyridyl $Os^{2+}$, $Fe^{2+}$ or $R^{2+}$ complex of the general formula I:

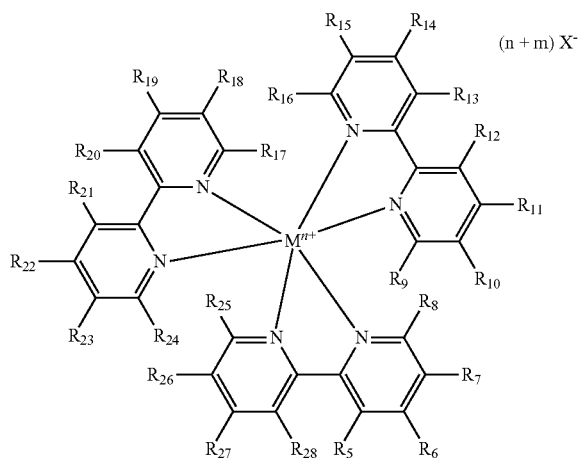

wherein M is Os, Fe or Ru; n is the formal oxidation state of the osmium, iron or ruthenium, wherein n is 2 or 3;

m is the positive charge of the tris-bipyridyl ligand, wherein m is an integer from 0 to 24, X is a counter anion selected from $Br^-$, $Cl^-$, $F^-$, $I^-$, $PF_6^-$, $BF_4^-$, $OH^-$, $ClO_4^-$, $SO_3^-$ $CF_3COO^-$, $CN^-$, alkyl$COO^-$, aryl$COO^-$ or a combination thereof;

$R_5$ to $R_{28}$ is each independently hydrogen, halogen, hydroxyl, azido, nitro, cyano, amino, substituted amino, thiol, $C_1$-$C_{10}$ alkyl, cycloalkyl, heterocycloalkyl, haloalkyl, aryl, heteroaryl, alkoxy, alkenyl, alkynyl, carboxamido, substituted carboxamido, carboxyl, protected carboxyl, protected amino, sulfonyl, substituted aryl, substituted cycloalkyl or substituted heterocycloalkyl, wherein at least one of said $R_5$ to $R_{28}$ is a group A or B:

wherein group A is

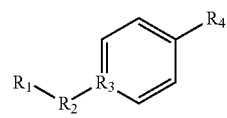

wherein group A is linked to the ring structure of the compound of general formula I via $R_4$;

$R_4$ is cis/trans C=C, C≡C, N=N, C=N, N=C, C—N, N—C, alkylene, arylene or a combination thereof;

$R_3$ is C or N;

$R_2$ is absent or is hydrogen, alkyl, alkylene, aryl, arylene, OH, O-alkyl, O-alkylene or a combination thereof;

$R_1$ is absent or is hydrogen, trialkoxysilane, trihalidesilane, thiol, COOH, $COO^-$, $Si(OH)_3$ or phosphonate;

group B is $-O(CH_2)_p-R_{29}$ linked to the ring structure of the compound of general formula I via the oxygen, wherein p is an integer from 9 to 12;

$R_{29}$ is hydrogen, trialkoxysilane, trihalidesilane, thiol, COOH, $COO^-$, $Si(OH)_3$ or phosphonate; and any two vicinal $R_5$-$R_{28}$ substituents, together with the carbon atoms to which they are attached, may form a fused ring system selected from cycloalkyl, heterocycloalkyl, heteroaryl or aryl, wherein said fused system may be substituted by one or more groups selected from $C_1$-$C_{10}$ alkyl, aryl, azido, cycloalkyl, halogen, heterocycloalkyl, alkoxy, hydroxyl, haloalkyl, heteroaryl, alkenyl, alkynyl, nitro, cyano, amino, substituted amino, carboxamido, substituted carboxamido, carboxyl, protected carboxyl, protected amino, thiol, sulfonyl or substituted aryl; and said fused ring system may also contain at least one heteroatom selected from the group consisting of N, O and S.

2. The method of claim 1, wherein said pyridyl complex is the compound of the general formula I, wherein:

(i) M is Os, Fe or Ru, n is 2, m is 0, X is $PF_6^-$ or $I^-$, $R_5$, $R_7$ to $R_{26}$ and $R_{28}$ each is hydrogen, $R_6$ is methyl, and $R_{27}$ is A, wherein $R_4$ is C=C, $R_3$ is N, and $R_2$ and $R_1$ are both absent (compounds 4a-4b, 5a-5b and 6a-6b, respectively);

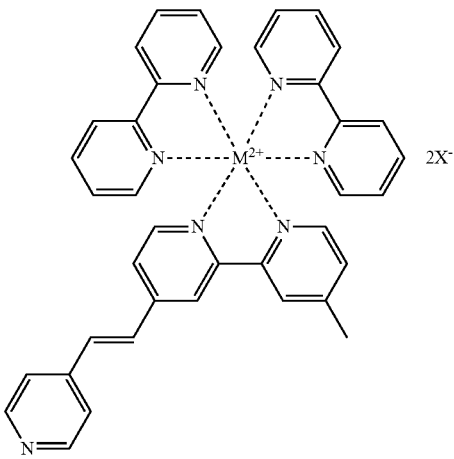

4a - M = Os; X = $PF_6^-$
4b - M = Os; X = $I^-$
5a - M = Fe; X = $PF_6^-$
5b - M = Fe; X = $I^-$
6a - M = Ru; X = $PF_6^-$
6b - M = Ru; X = $I^-$ (ii) M is Os, Fe or Ru, n is 2, m is 1, X is $PF_6^-$ or $I^-$, $R_5$, $R_7$ to $R_{26}$ and $R_{28}$ each is hydrogen, $R_6$ is methyl, and $R_{27}$ is A, wherein $R_4$ is C=C, $R_3$ is N, $R_2$ is methyl, and $R_1$ is absent (compounds 7a-7b, 8a-8b and 9a-9b, respectively);

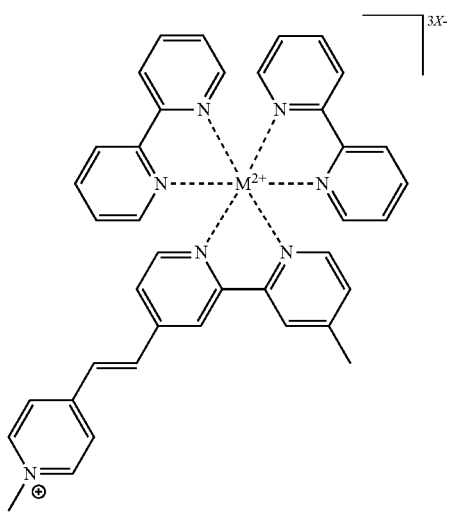

7a - M = Os; X = PF$_6^-$
7b - M = Os; X = I$^-$
8a - M = Fe; X = PF$_6^-$
8b - M = Fe; X = I$^-$
9a - M = Ru; X = PF$_6^-$
9b - M = Ru; X = I$^-$ (iii) M is Os, n is 2, m is 1, X is PF$_6^-$ or I$^-$, R$_5$, R$_7$ to R$_{26}$ and R$_{28}$ each is hydrogen, R$_6$ is methyl, and R$_{27}$ is A, wherein R$_4$ is C=C, R$_3$ is N, R$_2$ is propyl, and R$_1$ is trimethoxysilane (compounds 10a and 10b, respectively);

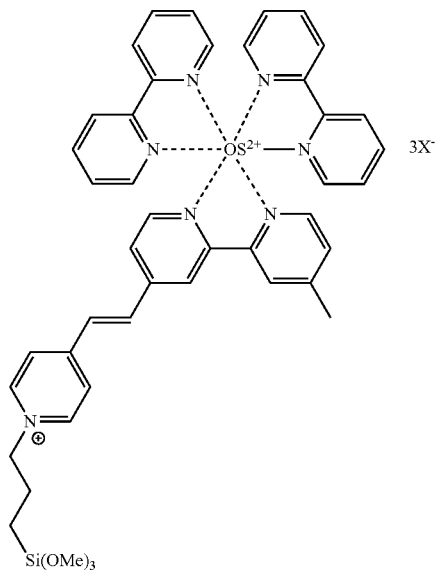

10a - X = PF$_6^-$
10b - X = I$^-$ (iv) M is Os, Fe or Ru, n is 2, m is 0, X is PF$_6^-$ or I$^-$, R$_5$, R$_7$ to R$_{26}$ and R$_{28}$ each is hydrogen, R$_6$ is methyl, and R$_{27}$ is A, wherein R$_4$ is C=C, R$_3$ is C, R$_2$ is OH, and R$_1$ is absent (compounds 11a-11b, 12a-12b and 13a-13b, respectively);

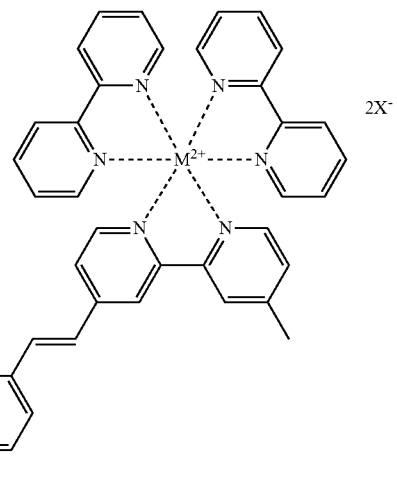

11a - M = Os; X = PF$_6^-$
11b - M = Os; X = I$^-$
12a - M = Fe; X = PF$_6^-$
12b - M = Fe; X = I$^-$
13a - M = Ru; X = PF$_6^-$
13b - M = Ru; X = I$^-$ (v) M is Os, n is 2, m is 0, X is PF$_6^-$ or I$^-$, R$_5$, R$_7$ to R$_{26}$ and R$_{28}$ each is hydrogen, R$_6$ is methyl, and R$_{27}$ is A, wherein R$_4$ is C=C, R$_3$ is C, R$_2$ is O-propyl, and R$_1$ is trimethoxysilane (compounds 14a and 14b, respectively); or

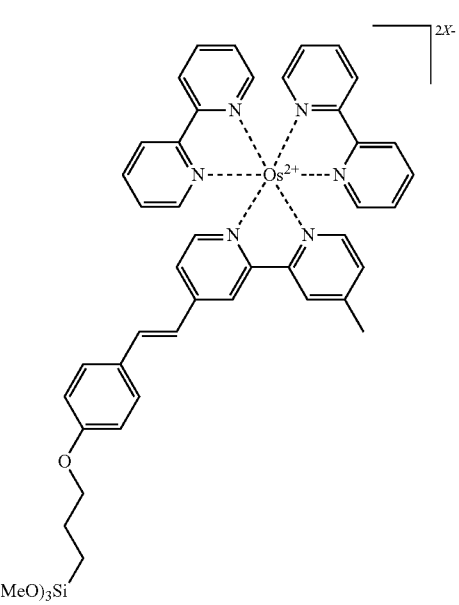

14a - X = PF$_6^-$
14b - X = I$^-$ (vi) M is Os, n is 2, m is 0, X is PF$_6^-$ or I$^-$, R$_5$, R$_7$ to R$_{26}$ and R$_{28}$ each is hydrogen, R$_6$ and R$_{27}$ each is B, wherein p is 9 and R$_{29}$ is triethoxysilane (compounds 15a and 15b, respectively).

15a - X = PF$_6^-$
15b - X = I$^-$

3. The method of claim 1, wherein, in step (i), said pyridyl complex is carried as a layered structure on a substrate.

4. The method of claim 1, wherein said pyridyl complex is carried as a layered structure on a substrate, or wherein said liquid sample is obtained as a result of treating a solid sample by a liquid media.

5. The method of claim 4, wherein said substrate is glass, said pyridyl complex is the compound of the general formula I wherein M is Os, n is 2, m is 1, X is PF$_6^-$ or I$^-$, R$_5$, R$_7$ to R$_{26}$ and R$_{28}$ each is hydrogen, R$_6$ is methyl, and R$_{27}$ is A, wherein R$_4$ is C=C, R$_3$ is N, R$_2$ is propyl, and R$_1$ is trimethoxysilane (compounds 10a and 10b, respectively), and a monolayer of said pyridyl complex is covalently bound to said substrate.

6. The method of claim 4, wherein:
 (i) said layered structure comprises a monolayer of said pyridyl complex, or a plurality of identical or different layers of said pyridyl complex;
 (ii) said pyridyl complex is bound to a linker designed to covalently bind to the surface of said substrate; or
 (iii) the surface of said substrate carries a functional group capable of coordinating or binding to said layered structure.

7. The method of claim 6, wherein said functional group is capable of either covalently or non-covalently binding to said layered structure.

8. The method of claim 4, wherein:
 (i) said substrate is hydrophilic, hydrophobic or a combination thereof;
 (ii) said substrate includes a material selected from glass, a doped glass, indium tin oxide (ITO)-coated glass, silicon, a doped silicon, Si(100), Si(111), SiO$_2$, SiH, silicon carbide mirror, quartz, a metal, metal oxide, a mixture of metal and metal oxide, group IV elements, mica, a polymer such as polyacrylamide and polystyrene, a plastic, a zeolite, a clay, wood, a membrane, an optical fiber, a ceramic, a metalized ceramic, an alumina, an electrically-conductive material, a semiconductor, steel or a stainless steel; or
 (iii) said substrate is optically transparent to the UV and visible spectral ranges.

9. The method of claim 8, wherein said substrate is hydrophilic, hydrophobic or a combination thereof; wherein said substrate is in the form of beads, microparticles, nanoparticles, quantum dots or nanotubes.

10. The method of claim 1, wherein said pyridyl complex is Os$^{2+}$-based pyridyl complex.

11. The method of claim 10, wherein said pyridyl complex is further capable of changing its oxidation state in response to a reduction of Fe$^{3+}$ at neutral pH, for detection of Fe$^{3+}$.

12. The method of claim 10, wherein:
 (i) a decrease of the metal to ligand charge transfer (MLCT) bands at λ=516 and 692 nm indicates the presence of Cr$^{6+}$, and the percentage of said decrease is proportional to the concentration of Cr$^{6+}$ in said sample; or
 (ii) said Os$^{2+}$-based pyridyl complex is exposed to said sample at a pH in a range of 0.1-3, and said sufficient time period is about 1 min.

13. The method of claim 12, wherein said Os$^{2+}$-based pyridyl complex is exposed to said sample at a pH range of 0.3-2.

14. The method of claim 13, wherein said Os$^{2+}$-based pyridyl complex is exposed to said sample at a pH of about 1.

15. The method of claim 1, wherein said pyridyl complex is comprised in an acidic aqueous solution.

16. The method of claim 15, wherein said solution has pH at a range of 0.1-3.

17. The method of claim 16, wherein said solution has a pH at a range of 0.3-2.

18. The method of claim 17, wherein said solution has a pH of about 1.

19. A method for detoxification of Cr$^{6+}$ in an aqueous or organic liquid media, comprising:
 (i) contacting said liquid media with a divalent osmium (Os$^{2+}$)-, iron (Fe$^{2+}$)- or ruthenium (Ru$^{2+}$)-based pyridyl complex capable of changing its oxidation state to Os$^{3+}$-, Fe$_3^+$- or Ru$_3^+$-based pyridyl complex, respectively, in response to a reduction of Cr$^{6+}$, for a sufficient time period at the presence of H$^+$, wherein said pyridyl complex is carried as a layered structure on a substrate;
 (ii) monitoring the presence of Cr$^{6+}$ and determining its concentration in a sample taken from said liquid media; and
 when Cr$^{6+}$ is detected in said sample, reducing said Os$^{3+}$-, Fe$^{3+}$- or Ru$^{3+}$-based pyridyl complex and repeating steps (i) and (ii) wherein said pyridyl complex is a charged tris-bipyridyl Os$^{2+}$, Fe$^{2+}$ or Ru$^{2+}$ complex of the general formula I:

wherein M is Os, Fe or Ru; n is the formal oxidation state of the osmium, iron or ruthenium,
wherein n is 2 or 3;
m is the positive charge of the tris-bipyridyl ligand, wherein m is an integer from 0 to 24,
X is a counter anion selected from Br$^-$, Cl$^-$, F$^-$, I$^-$, PF$_6^-$, BF$_4^-$, OH$^-$, ClO$_4^-$, SO$_3^-$, CF$_3$COO$^-$, CN$^-$, alkylCOO$^-$, arylCOO$^-$ or a combination thereof;
R$_5$ to R$_{28}$ is each independently hydrogen, halogen, hydroxyl, azido, nitro, cyano, amino, substituted amino, thiol, $C_1$-$C_{10}$ alkyl, cycloalkyl, heterocycloalkyl, haloalkyl, aryl, heteroaryl, alkoxy, alkenyl, alkenyl, carboxamido, substituted carboxamido, carboxyl, protected carboxyl, protected amino, sulfonyl, substituted aryl, substituted cycloalkyl or substituted heterocycloalkyl, wherein at least one of said $R_5$ to $R_{28}$ is a group A or B: wherein group A is

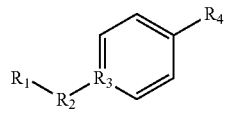

wherein
group A is linked to the ring structure of the compound of general formula I via $R_4$;
- $R_4$ is cis/trans C=C, C≡C, N=N, C=N, N=C, C—N, N—C, alkylene, arylene or a combination thereof;
- $R_3$ is C or N;
- $R_2$ is absent or is hydrogen, alkyl, alkylene, aryl, arylene, OH, O-alkyl, O-alkylene or a combination thereof;
- $R_1$ is absent or is hydrogen, trialkoxysilane, trihalidesilane, thiol, COOH, COO$^-$, Si(OH)$_3$ or phosphonate;
- group B is —O(CH$_2$)$_p$—$R_{29}$ linked to the ring structure of the compound of general formula I via the oxygen, wherein p is an integer from 9 to 12;
- $R_{29}$ is hydrogen, trialkoxysilane, trihalidesilane, thiol, COOH, COO$^-$, Si(OH)$_3$ or phosphonate; and any two vicinal $R_5$-$R_{28}$ substituents, together with the carbon atoms to which they are attached, may form a fused ring system selected from cycloalkyl, heterocycloalkyl, heteroaryl or aryl, wherein said fused system may be substituted by one or more groups selected from $C_1$-$C_{10}$ alkyl, aryl, azido, cycloalkyl, halogen, heterocycloalkyl, alkoxy, hydroxyl, haloalkyl, heteroaryl, alkenyl, alkynyl, nitro, cyano, amino, substituted amino, carboxamido, substituted carboxamido, carboxyl, protected carboxyl, protected amino, thiol, sulfonyl or substituted aryl; and said fused ring system may also contain at least one heteroatom selected from the group consisting of N, O and S.

20. The method of claim 19, wherein said substrate is in the form of beads, nanoparticles, quantum dots or nanotubes; or the monitoring of the presence of Cr$^{6+}$ and the determination of its concentration in step (ii) is carried out by flame atomic absorption spectrometry (FAAS), inductively coupled plasma atomic emission spectrometry (ICP-AES), chemiluminescence, X-ray fluorescence, electrochemical methods.

21. The method of claim 19, wherein said pyridyl complex is Os$^{2+}$-based pyridyl complex.

22. The method of claim 21, wherein said liquid media is contacted with said Os$^{2+}$-based pyridyl complex is contacted with said liquid media at a pH in a range of 0.1-3.

23. The method of claim 22, wherein said liquid media is contacted with said Os$^{2+}$-based pyridyl complex at a pH in a range of 0.3-2.

24. The method of claim 23, wherein said liquid media is contacted with said Os$^{2+}$-based pyridyl complex at a pH of about 1.

25. A method for detoxification of Cr$^{6+}$ in an aqueous or organic liquid media, comprising contacting said liquid media with a divalent osmium (Os$^{2+}$)-, iron (Fe$_2^+$)- or ruthenium (Ru$_2^+$)-based pyridyl complex capable of changing its oxidation state to Os$^{3+}$-, Fe$^{3+}$- or Ru$^{3+}$-based pyridyl complex, respectively, in response to a reduction of Cr$^{6+}$, for a sufficient time period at the presence of H$^+$, wherein said pyridyl complex is carried as a layered structure on a substrate wherein said pyridyl complex is a charged tris-bipyridyl Os$^{2+}$, Fe$^{2+}$ or Ru$^{2+}$ complex of the general formula I:

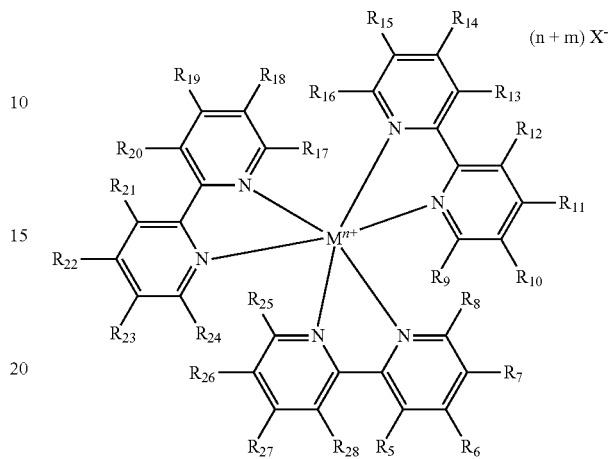

wherein M is Os, Fe or Ru; n is the formal oxidation state of the osmium, iron or ruthenium,
- wherein n is 2 or 3;
- m is the positive charge of the tris-bipyridyl ligand, wherein m is an integer from 0 to 24,
- X is a counter anion selected from Br$^-$, Cl$^-$, F$^-$, I$^-$, PF$_6^-$, BF$_4^-$, OH$^-$, OH$_4^-$, SO$_3^-$, CF$_3$COO$^-$, CN$^-$, alkylCOO$^-$, arylCOO$^-$ or a combination thereof;
- $R_5$ to $R_{28}$ is each independently hydrogen, halogen, hydroxyl, azido, nitro, cyano, amino, substituted amino, thiol, $C_1$-$C_{10}$ alkyl, cycloalkyl, heterocycloalkyl, haloalkyl, aryl, heteroaryl, alkoxy, alkenyl, alkynyl, carboxamido, substituted carboxamido, carboxyl, protected carboxyl, protected amino, sulfonyl, substituted aryl, substituted cycloalkyl or substituted heterocycloalkyl, wherein at least one of said $R_5$ to $R_{28}$ is a group A or B: wherein group A is

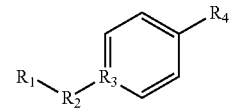

wherein
group A is linked to the ring structure of the compound of general formula I via $R_4$;
- $R_4$ is cis/trans C=C, C≡C, N=N, C=N, N=C, C—N, N—C, alkylene, arylene or a combination thereof;
- $R_3$ is C or N;
- $R_2$ is absent or is hydrogen, alkyl, alkylene, aryl, arylene, OH, O-alkyl, O-alkylene or a combination thereof;
- $R_1$ is absent or is hydrogen, trialkoxysilane, trihalidesilane, thiol, COOH, COO$^-$, Si(OH)$_3$ or phosphonate;
- group B is —O(CH$_2$)$_p$—$R_{29}$ linked to the ring structure of the compound of general formula I via the oxygen, wherein p is an integer from 9 to 12;
- $R_{29}$ is hydrogen, trialkoxysilane, trihalidesilane, thiol, COOH, COO$^-$, Si(OH)$_3$ or phosphonate; and any two vicinal $R_5$-$R_{28}$ substituents, together with the carbon atoms to which they are attached, may form a fused ring system selected from cycloalkyl, heterocycloalkyl, heteroaryl or aryl, wherein said fused system may be substituted by one or more groups selected from $C_1$-$C_{10}$ alkyl, aryl, azido, cycloalkyl, halogen, heterocycloalkyl, alkoxy, hydroxyl, haloalkyl, heteroaryl, alkenyl, alkynyl, nitro, cyano, amino, substituted amino, carboxamido, substituted carboxamido, carboxyl, protected carboxyl, protected amino, thiol, sulfonyl or substituted aryl; and said fused ring system may also contain at least one heteroatom selected from the group consisting of N, O and S.

26. A catalytic process for reduction of $Cr^{6+}$, comprising reducing said $Cr^{6+}$ with a divalent osmium ($Os^{2+}$)-based pyridyl complex of the general formula I:

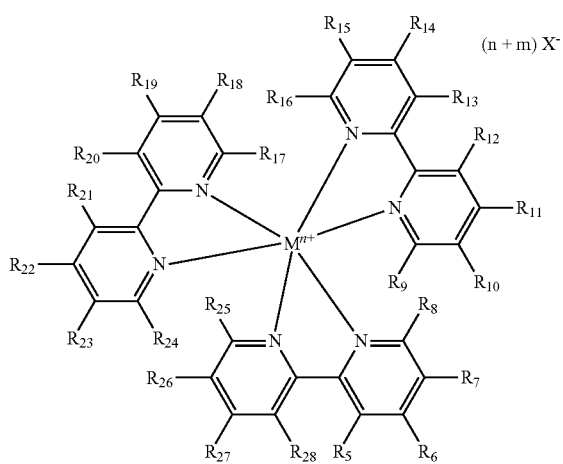

wherein M is Os; n is the formal oxidation state of the osmium, iron or ruthenium, wherein n is 2 or 3; m is the positive charge of the tris-bipyridyl ligand, wherein m is an integer from 0 to 24, X is a counter anion selected from $Br^-$, $Cl^-$, $F^-$, $I^-$, $PF_6^-$, $BF_4^-$, $OH^-$, $ClO_4^-$, $SO_3^-$, $CF_3COO^-$, $CN^-$, alkylCOO$^-$, arylCOO$^-$ or a combination thereof; and $R_5$ to $R_{28}$ is each independently hydrogen, halogen, hydroxyl, azido, nitro, cyano, amino, substituted amino, thiol, $C_1$-$C_{10}$ alkyl, cycloalkyl, heterocycloalkyl, haloalkyl, aryl, heteroaryl, alkoxy, alkenyl, alkynyl, carboxamido, substituted carboxamido, carboxyl, protected carboxyl, protected amino, sulfonyl, substituted aryl, substituted cycloalkyl or substituted heterocycloalkyl, wherein at least one of said $R_5$ to $R_{28}$ is a group A or B:

wherein group A is

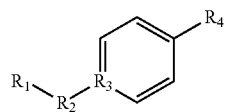

and wherein
group A is linked to the ring structure of the compound of general formula I via $R_4$;
$R_4$ is cis/trans C=C, C≡C, N=N, C=N, N=C, C—N, N—C, alkylene, arylene or a combination thereof;
$R_3$ is C or N;
$R_2$ is absent or is hydrogen, alkyl, alkylene, aryl, arylene, OH, O-alkyl, O-alkylene or a combination thereof;
$R_1$ is absent or is hydrogen, trialkoxysilane, trihalidesilane, thiol, COOH, COO$^-$, Si(OH)$_3$ or phosphonate;
group B is —O(CH$_2$)$_p$—$R_{29}$ linked to the ring structure of the compound of general formula I via the oxygen, wherein p is an integer from 9 to 12;
$R_{29}$ is hydrogen, trialkoxysilane, trihalidesilane, thiol, COOH, COO$^-$, Si(OH)$_3$ or phosphonate;
any two vicinal $R_5$-$R_{28}$ substituents, together with the carbon atoms to which they are attached, may form a fused ring system selected from cycloalkyl, heterocycloalkyl, heteroaryl or aryl, wherein said fused system may be substituted by one or more groups selected from $C_1$-$C_{10}$ alkyl, aryl, azido, cycloalkyl, halogen, heterocycloalkyl, alkoxy, hydroxyl, haloalkyl, heteroaryl, alkenyl, alkynyl, nitro, cyano, amino, substituted amino, carboxamido, substituted carboxamido, carboxyl, protected carboxyl, protected amino, thiol, sulfonyl or substituted aryl; and said fused ring system may also contain at least one heteroatom selected from the group consisting of N, O and S,
to thereby oxidize the $Os^{2+}$ to $Os^{3+}$, and exposing the oxidized $Os^{3+}$ to water for a sufficient time period to thereby regenerate the $Os^{3+}$ to $Os^{2+}$.

* * * * *